(12) United States Patent
Hillman et al.

(10) Patent No.: US 6,228,991 B1
(45) Date of Patent: May 8, 2001

(54) GROWTH-ASSOCIATED PROTEASE INHIBITOR HEAVY CHAIN PRECURSOR

(75) Inventors: Jennifer L. Hillman, Mountain View; Karl J. Guegler, Menlo Park; Chandra Patterson, Mountain View, all of CA (US)

(73) Assignee: Incyte Genomics, Inc., Palo Alto, CA (US)

( * ) Notice: Subject to any disclaimer, the term of this patent is extended or adjusted under 35 U.S.C. 154(b) by 0 days.

(21) Appl. No.: 09/388,774

(22) Filed: Sep. 2, 1999

Related U.S. Application Data

(62) Division of application No. 09/074,579, filed on May 7, 1998, now Pat. No. 6,001,596.

(51) Int. Cl.$^7$ ............................. C07K 14/00; A61K 37/18
(52) U.S. Cl. ................................................. 530/350; 514/2
(58) Field of Search ................................. 530/350; 514/2

(56) References Cited

U.S. PATENT DOCUMENTS 5,166,133 * 11/1992 Houston et al. ........................ 514/8

OTHER PUBLICATIONS

Benyon, R.J. and Bond, J.S. (1994) *Proteolytic Enzymes: A Practical Approach*, Oxford University Press, New York. NY, pp. 1–5.

Daveau, M. et al., "Hepatic and Extra–hepatic Transcription of Inter–α–inhibitor Family Genes under Normal or Acute Inflammatory Conditions in Rat", *Arch. Biochem. Biophys.* 350:315–323 (1998).

Salier, J.P. et al., "The Genes for the Inter–α–inhibitor Family Share a Homologous Organization in Human and Mouse", *Mamm.Genome* 2:233–239 (1992).

Salier, J. P. "Inter–α–trypsin Inhibitor: Emergence of Family within the Kunitz–type Protease Inhibitor Superfamily", *Trends Biochem. Sci.* 15:435–439 (1990).

Broze, G. J., "Tissue Factor Pathway Inhibitor and the Revised Theory of Coagulation", *Annu.Rev.Med.* 46:103–112 (1995).

Wagner, S. L. et al., "Co–distribution of Protease Nexin–1 and Protease Nexin–2 in Brains of Non–human Primates", *Brain Res.* 626:90–98 (1993).

Bourguignon, J. et al., "Human Pre–α–trypsin Inhibitor––precursor Heavy Chain cDNA and Deduced Amino–acid Sequence", *Eur. J. Biochem.* 212:771–776 (1993).

Salier, J.P. et al., "The Inter–α–inhibitor Family: from Structure to Regulation", *Biochem. J.* 315:1–9 (1996).

Huizinga, E.G. et al., "Crystal Structure of the A3 Domain of Human von Willebrand Factor: Implications for Collagen Binding", *Structure* 5:1147–1156 (1997).

Murphy, G., "The Regulation of Connective Tissue Metalloproteinases by Natural Inhibitors", *Agents Actions Suppl.* 35:69–76 (1991).

Pakyz, A and Isreal, D., "Overview of Protease Inhibitors", *J.Am. Pharm.Assoc.* (Wash.) NS37:543–551 (1997).

Gebhard, W. et al., (GI 33985), GenBank Sequences Database (Accession X07173), National Center for Biotechnology Information, National Library of Medicine, Bethesda, Maryland 20894. (1997).

Diarra–Mehrpour, M., (GI 33989), GenBank Sequence Database (Accession X63652), National Center for Biotechnology Information, National Library of Medicine, Bethesda, Maryland 20894. (1997).

Bourguignon, J., (GI 288563), GenBank Sequence Database (Accession X67055), National Center for Biotechnology Information, National Library of Medicine, Bethesda, Maryland 20894. (1993).

Beynon, R.J. and Bond, J.S. (1994) *Proteolytic Enzymes: A Practical Approach*, Oxford University Press, New York. NY, pp. 25–55.

Hillier, L. et al., GenBank Database, Accession No. AA134751 (5/1997).

Muragaki, Y. et al., EMBL Database, Accession No. M32137 (11/1994).

Hillier et al.: "WashU–Merck EST Project 1997" EMBL Sequence Database, May 19, 1997 (1997–05–19), XP002120517 Heidelberg DE, Ac AA393894.

Hillier et al.: "The WashU–Merck EST Project", EMBL Sequence Database, Dec. 9, 1996, (1996–12–09), XP002120518, Heidelberg DE, Ac AA134750.

Hillier et al.: "WashU–Merck EST Project" EMBL Sequence Database, May 19, 1997 (1997–05–19), XP002120519, Heidelberg DE, Ac AA393810.

* cited by examiner

Primary Examiner—Ponnathapu Achutamurthy
Assistant Examiner—Peter P. Tung
(74) Attorney, Agent, or Firm—Incyte Genomics, Inc.

(57) ABSTRACT

The invention provides a human growth-associated protease inhibitor heavy chain precursor (GAPIP) and polynucleotides which identify and encode GAPIP. The invention also provides expression vectors, host cells, antibodies, agonists, and antagonists. The invention also provides methods for diagnosing, treating or preventing disorders associated with expression of GAPIP.

6 Claims, 18 Drawing Sheets

FIGURE 1A

```
                 9        18        27        36        45        54
5'  C  CCT GAG AGC GTC CCG CAG TGG CTG GAG CCC CAA ACG TGT CCC 63        72        81        90        99       108
    GCC GGG TCC CCG AGC GTC CCG CGC CCC ATG CTC CTG CTG GGG
                                         M   L   L   L   G 117       126       135       144       153       162
    CTG TGC CTG GGG CTG TCC CTG TGT GGG CAG GCG CAG AGC TGG
     L   C   L   G   L   S   L   C   G   Q   A   Q   S   W 171       180       189       198       207       216
    GGC CAC TCT TCG GAG CAG GAT GGA CTC AGG CAA GTC CAG AGA CTG TTG
     G   H   S   S   E   Q   D   G   L   R   Q   V   P   R   L   L 225       234       243       252       261       270
    CAG AGG CTG AAA ACC CCT TTG ATG ACA GAA TTC TCA GTG AAG TCT ACC ATC
     Q   R   L   K   T   P   L   M   T   E   F   S   V   K   S   T   I 279       288       297       306       315       324
    ATT TCC CGT TAT GCC TTC ACT ACG GTT TCC TGC AGA ATG CTG AAC AGA GCT TCT
     I   S   R   Y   A   F   T   T   V   S   C   R   M   L   N   R   A   S 333       342       351       360       369       378
    GAA GAC CAG GAC ATT GAG TTC CAG ATG CAG ATT CCA GCT GCA GCT TTC ATC ACC
     E   D   Q   D   I   E   F   Q   M   Q   I   P   A   A   A   F   I   T
```

```
       387 396     405     414     423     432
AAC TTC ACT ATG CTT ATT GGA GAC AAG GTG TAT CAG GGC GAA ATT ACA GAG AGA
 N   F   T   M   L   I   G   D   K   V   Y   Q   G   E   I   T   E   R 441 450     459     468     477     486
GAA AAG AGT GGT GAT AGG GTA AAA GAG AAA AGG AAT ACC ACA GAA GAA
 E   K   S   G   D   R   V   K   E   K   R   N   T   T   E   E 495 504     513     522     531     540
AAT GGA GAG AAG GGG ACT GAA ATA TTC AGA GCT TCT GCA GTG ATT CCC AGC AAG
 N   G   E   K   G   T   E   I   F   R   A   S   A   V   I   P   S   K 549 558     567     576     585     594
GAC GCC GCC TTT CTG AGT TAT GAG GAG CTT CAG CTG CAG CTG TCT GCA GTG ATT CCC AGC AAG
```



```
       387 396     405     414     423     432
AAC TTC ACT ATG CTT ATT GGA GAC AAG GTG TAT CAG GGC GAA ATT ACA GAG AGA
 N   F   T   M   L   I   G   D   K   V   Y   Q   G   E   I   T   E   R 441 450     459     468     477     486
GAA AAG AGT GGT GAT AGG GTA AAA GAG AAA AGG AAT ACC ACA GAA GAA
 E   K   S   G   D   R   V   K   E   K   R   N   T   T   E   E 495 504     513     522     531     540
AAT GGA GAG AAG GGG ACT GAA ATA TTC AGA GCT TCT GCA GTG ATT CCC AGC AAG
 N   G   E   K   G   T   E   I   F   R   A   S   A   V   I   P   S   K 549 558     567     576     585     594
GAC GCC GCC TTT CTG AGT TAT GAG GAG CTT CAG CTG CAG CTG TCT GCA GTG CGC CTG GGC
 D   K   A   F   L   S   Y   E   E   L   Q   L   Q   L   S   A   V   R   L   G 603 612     621     630     639     648
AAG TAC GAG CAC AGC ATC AGC GTG CGG CCC CAG CAG CTG TCC CTG GAG AGG AGG CTG AGC
 K   Y   E   H   S   I   S   V   R   P   Q   Q   L   S   L   E   R   R   L   S 657 666     675     684     693     702
GTG GAC GTG AAT ATC CTG GAG AGC GCC GGC ATC GCA TCC CTG GAG GTG CTG CCG
 V   D   V   N   I   L   E   S   A   G   I   A   S   L   E   V   L   P 711 720     729     738     747     756
CTT CAC AAC AGC AGG CAG AGG GGC AGT GGG CGC GGG GAA GAT TCT GGG CCT
 L   H   N   S   R   Q   R   G   S   G   R   G   E   D   D   S   G   P
```

FIGURE 1B

```
       765            774       783            792       801            810
CCC CCA TCT ACT GTC ATT AAC CAA AAT GAA ACA TTT GCC AAC ATA ATT TTT AAA
 P   P   S   T   V   I   N   Q   N   E   T   F   A   N   I   I   F   K 819            828       837            846       855            864
CCT ACT GTA GTA CAA CAA GCC AGG ATT GCC CAG AAT GGA ATT TTG GGA GAC TTT
 P   T   V   V   Q   Q   A   R   I   A   Q   N   G   I   L   G   D   F 873            882       891            900       909            918
ATC ATT AGA TAT GAC GTC AAT AGA GAA CAG AGC ATT GGG GAC ATC CAG GTT CTA
 I   I   R   Y   D   V   N   R   E   Q   S   I   G   D   I   Q   V   L 927            936       945            954       963            972
AAT GGC TAT TTT GTG CAC TAC TTT GCT CCT AAA GAC CTT CCT TTA CCC AAG
 N   G   Y   F   V   H   Y   F   A   P   K   D   L   P   L   P   K 981            990       999            1008      1017           1026
AAT GTG GTA TTC GTG CTT GAC AGC AGT GCT TCT ATG GTG GGA ACC AAA CTC CGG
 N   V   V   F   V   L   D   S   S   A   S   M   V   G   T   K   L   R 1035           1044      1053           1062      1071           1080
CAG ACC AAG GAT GCC CTC CTC ACA ATT CTC CAT GAC CTC CGA CCC CAG GAC CGT
 Q   T   K   D   A   L   L   T   I   L   H   D   L   R   P   Q   D   R 1089           1098      1107           1116      1125           1134
TTC AGT ATC ATT GGA TTT TCC AAC CGG ATC AAA GTA TGG AAG GAC CAC TTG ATA
 F   S   I   I   G   F   S   N   R   I   K   V   W   K   D   H   L   I
```

FIGURE 1C

```
      1143           1152            1161           1170            1179           1188
TCA GTC ACT CCA GAC AGC ATC AGG GAT GGG AAA GTG TAC ATT CAC CAT ATG TCA
 S   V   T   P   D   S   I   R   D   G   K   V   Y   I   H   H   M   S 1197           1206            1215           1224            1233           1242
CCC ACT GGA GGC ACA GAC ATC AAC GGG GCC CTG CAG AGG GCC ATC AGG CTC CTC
 P   T   G   G   T   D   I   N   G   A   L   Q   R   A   I   R   L   L 1251           1260            1269           1278            1287           1296
AAC AAG TAC GTG GCC CAC AGT GGA ATT GGA GAC CGG AGC GTG TCC CTC ATC GTC
 N   K   Y   V   A   H   S   G   I   G   D   R   S   V   S   L   I   V 1305           1314            1323           1332            1341           1350
TTC CTG ACG GAT GGG AAG CCC ACG GTC GGG GAG ACG CAC ACC ATC AAG ATC CTC
 F   L   T   D   G   K   P   T   V   G   E   T   H   T   I   K   I   L 1359           1368            1377           1386            1395           1404
AAC ACC CGA GAG GCC GCC CGA GGC CAA GTC TGC ATC TTC ACC ATT GGC ATC
 N   T   R   E   A   A   R   G   Q   V   C   I   F   T   I   G   I 1413           1422            1431           1440            1449           1458
GGC GAC GAC TTC AGG CTG CTG GAG AAA CTG TCG CTG GAG AAC TGT GGC
 G   D   D   F   R   L   L   E   K   L   S   L   E   N   C   G 1467           1476            1485           1494            1503           1512
CTC ACA CGG CGC GTG CAC GAG GAG GAG GAC GCA GGC TCG CAG CTC ATC GGG TTC
 L   T   R   R   V   H   E   E   E   D   A   G   S   Q   L   I   G   F
```

```
     1521            1530            1539            1548            1557            1566
TAC  GAT  GAA  ATC  AGG  ACC  CCG  CTC  CTC  TCT  GAC  ATC  CGC  ATC  GAT  TAT  CCC  CCC
 Y    D    E    I    R    T    P    L    L    S    D    I    R    I    D    Y    P    P 1575            1584            1593            1602            1611            1620
AGC  TCA  GTG  GTG  CAG  GCC  ACC  AAG  GCC  CTG  TTC  CCC  AAC  TAC  TTC  AAC  GGC  TCG
 S    S    V    V    Q    A    T    K    A    L    F    P    N    Y    F    N    G    S 1629            1638            1647            1656            1665            1674
GAG  ATC  ATC  ATT  GCG  GGG  AAG  CTG  GTG  GAC  AGG  AAG  CTG  GAT  CAC  CTG  CAC  GTG
 E    I    I    I    A    G    K    L    V    D    R    K    L    D    H    L    H    V 1683            1692            1701            1710            1719            1728
GAG  GTC  ACC  GCC  AAC  AGT  AAG  AAA  TTC  ATC  ATC  CTG  AAG  ACA  GAT  GTG  CCT
 E    V    T    A    N    S    K    K    F    I    I    L    K    T    D    V    P 1737            1746            1755            1764            1773            1782
GTG  CGG  CCT  CAG  AAG  GCA  GGG  AAA  GAT  GTC  ACA  GGA  AGC  CCC  AGG  CCT  GGA  GGC
 V    R    P    Q    K    A    G    K    D    V    T    G    S    P    R    P    G    G 1791            1800            1809            1818            1827            1836
GAT  GGA  GAG  GGG  GAC  ACC  AAC  CAC  ATC  GAG  CGT  CTC  TGG  AGC  TAC  CTC  ACC  ACA
 D    G    E    G    D    T    N    H    I    E    R    L    W    S    Y    L    T    T 1845            1854            1863            1872            1881            1890
AAG  GAG  CTG  CTG  AGC  TCC  TGG  CTG  CAA  AGT  GAC  GAT  GAA  CCG  GAG  AAG  GAG  CGG
 K    E    L    L    S    S    W    L    Q    S    D    D    E    P    E    K    E    R
```

```
       1899          1908          1917          1926          1935          1944
CTG CGG CAG CGG GCC CAG GCC CTG GCT GTG AGC TAC CGC TTC CTC ACT CCC TTC
 L   R   Q   R   A   Q   A   L   A   V   S   Y   R   F   L   T   P   F 1953          1962          1971          1980          1989          1998
ACC TCC ATG AAG CTG AGG GGG CCG GTC CCA CGC ATG GAT GGC CTG GAG GAG GCC
 T   S   M   K   L   R   G   P   V   P   R   M   D   G   L   E   E   A 2007          2016          2025          2034          2043          2052
CAC GGC ATG TCG GCT GCC ATG GGA CCC GAA CCG GTG GTG CAG AGC GTG CGA GGA
 H   G   M   S   A   A   M   G   P   E   P   V   V   Q   S   V   R   G 2061          2070          2079          2088          2097          2106
GCT GGC ACG CAG CCA GGG CCT TTG CTC AAG AAG CCA TAC CAG CCA AGA ATT AAA
 A   G   T   Q   P   G   P   L   L   K   K   P   Y   Q   P   R   I   K 2115          2124          2133          2142          2151          2160
ATC TCT AAA ACA TCA GTG GAT GGT GAT CCC CAC TTT GTT GTG GAT TTC CCC CTG
 I   S   K   T   S   V   D   G   D   P   H   F   V   V   D   F   P   L 2169          2178          2187          2196          2205          2214
AGC ATG CTC ACC GTG TGC TTC AAC ATT GAT GGG CAG CCC GGG GAC ATC CTC AGG
 S   M   L   T   V   C   F   N   I   D   G   Q   P   G   D   I   L   R 2223          2232          2241          2250          2259          2268
AGC AGA GAC CAC AGG GAC TCT GAT CAC AGG GAC TCT GGT GTC ACA GTG AAC GGA GAG TTA ATT GGG
 S   R   D   H   R   D   S   D   H   R   D   S   G   V   T   V   N   G   E   L   I   G
```



```
       2223          2232          2241          2250          2259          2268
AGC AGA GAC CTC ACC GTG TGC TTC AAC ATT GAT GGG CAG CCC GGG GAC ATC CTC AGG
 S   R   D   L   T   V   C   F   N   I   D   G   Q   P   G   D   I   L   R 2223          2232          2241          2250          2259          2268
CTG GTC TCT GAT CAC AGG GAC TCT GGT GTC ACA GTG AAC GGA GAG TTA ATT GGG
 L   V   S   D   H   R   D   S   G   V   T   V   N   G   E   L   I   G
```

FIGURE 1F

```
        2277            2286            2295            2304            2313            2322
GCA CCC GCC CCT CCA AAT GGC CAC AAG AAA CAG CGC ACT TAC CGC ACT ATC
 A   P   A   P   P   N   G   H   K   K   Q   R   T   Y   R   T   I
        2331            2340            2349            2358            2367            2376
ACC ATC CTC ATC AAC AAG CCA GAG AGA TCT TAT CTC GAG ATC ACA CCG AGC AGA
 T   I   L   I   N   K   P   E   R   S   Y   L   E   I   T   P   S   R
        2385            2394            2403            2412            2421            2430
GTC ATC TTG GAT GGT GGG GAC AGA CTG GTG CTC CCC TGC AAC CAG AGT GTG GTG
 V   I   L   D   G   G   D   R   L   V   L   P   C   N   Q   S   V   V
        2439            2448            2457            2466            2475            2484
GTG GGG AGC TGG GGG CTG GAG GTG TCC GTG TCT GCC AAC GCC AAT GTC ACC GTC
 V   G   S   W   G   L   E   V   S   V   S   A   N   A   N   V   T   V
        2493            2502            2511            2520            2529            2538
ACC ATC CAG GGC TCC ATA GCC TTT GTC ATC CTC CAC CTC TAC AAA AAG CCG
 T   I   Q   G   S   I   A   F   V   I   L   H   L   Y   K   K   P
        2547            2556            2565            2574            2583            2592
GCG CCC TTC CAG CGA CAC CAC CTG GGT TTC TAC ATT GCC AAC AGC GAG GGC CTT
 A   P   F   Q   R   H   H   L   G   F   Y   I   A   N   S   E   G   L
        2601            2610            2619            2628            2637            2646
TCC AGC AAC TGC CAC GGA CTG CTG GGT CAG TTC CTG AAT CAG GAT GCC AGA CTC
 S   S   N   C   H   G   L   L   G   Q   F   L   N   Q   D   A   R   L
```

```
                    2655              2664              2673              2682              2691              2700
                    ACA GAA GAC       CCT GCA GGG       CCC AGC CAG       AAC CTC ACT       CAC CCT CTG       CTC CTT CAG
                     T   E   D         P   A   G         P   S   Q         N   L   T         H   P   L         L   L   Q 2709              2718              2727              2736              2745              2754
                    GTG GGA GAG       GGG CCT GAG       GCC GTC CTA       ACA GTG AAA       GGC CAC CAA       GTC CCA GTG
                     V   G   E         G   P   E         A   V   L         T   V   K         G   H   Q         V   P   V 2763              2772              2781              2790              2799              2808
                    GTC TGG AAG       CAA AGG AAG       ATT TAC AAC       GGG GAA GAG       CAG GAG ATA       GAC TGC TGG TTT
                     V   W   K         Q   R   K         I   Y   N         G   E   E         Q   E   I         D   C   W   F 2817              2826              2835              2844              2853              2862
                    GCC AGG AAC       AAT GCC GCC       AAA CTG ATT       GAC GGG GAG       TAC AAG GAT       TAC CTG GCA
                     A   R   N         N   A   A         K   L   I         D   G   E         Y   K   D         Y   L   A 2871              2880              2889              2898              2907              2916
                    TCC CAT CCA       TTT GAC ACA       GGG ATG ACA       CTT GGC ACA       GGG ATG TCC       AGG GAG CTC
                     S   H   P         F   D   T         G   M   T         L   G   R         G   M   S         R   E   L 2925              2934              2943              2952              2961              2970
                    TGA AGC TGG       CAG CCT TAA       AGA TGC AAG       GAC AAG GAC       AGT GAT GTG       GGG AGG
                     *   S   W         Q   P   *         R   C   K         D   K   D         S   D   V         G   R 2979              2988              2997              3006              3015              3024
                    CCG TGG GGC       AGC TCT TTT       CAT GGC TTG       TAC ACG CCT       CAG CTC CTG       GCA ATT AGC
                     P   W   G         S   S   F         H   G   L         Y   T   P         Q   L   L         A   I   S
```

```
      3033           3042           3051           3060           3069           3078
TGG ACT CCA CCC ACC CCT GGT GCA GCA TAG ATC CGA CGT CTG TCT GGG CGA
      3087           3096           3105           3114           3123           3132
AGG GTA GGG GTG GGT AGG GGC GGG AAG CCT GAG TGC AAA TGT CAT TTC CCT CTA
      3141           3150           3159           3168           3177           3186
CTG CCT CTT CCT GCC TCT CCC CAC CCT GCC CAC ATC CAC AGA GGG GAG AGA AGG
      3195           3204           3213           3222           3231           3240
GTC ATA GCT AAA TGC AAC AAA GTC TGT ATC TTG TCC CAA CCT GCT TTT CTG TTC
      3249           3258           3267           3276           3285           3294
TGT TAG CAT ATC ATA AAG TAA GCC TTT CTG GTG AAG GAA GGT TGC TAT GAA ACT
      3303           3312           3321           3330           3339           3348
TTT TTT CTT GGT GGA AAT GGC CAA GTT TAG GCA CTC TGC TTT TTG CCT TAC ACT
      3357           3366           3375           3384           3393           3402
AAT GCT TAG AAA GCT GTC TTT TCA GTG GTG TTG CAG CCC CCA GAT GTG TGG CCA
      3411           3420           3429           3438           3447           3456
ACC TCT GCT GCA AAG GAA TCT CTT GCT GAG TCC AGG CCA CCA ATC AGG CAA ATA
      3465           3474           3483           3492           3501           3510
GCC CAT ACA TTT GAT CGT TGT AAA CCA TGA AGT CTT TTC TTG CAA GAC GTT TTT
```

FIGURE 1I

```
     3519           3528           3537           3546           3555           3564
CTT CTG CTG TGG TAT CTT GCC CTT AAA AAT TAG TTT TCA TTA AAA AGA AAT TTG
     3573           3582           3591           3600           3609           3618
ATT GAA AAT TAA AAA AAA ATA AAA AAA AAA GAA AAA AAA GAA AGA AAA AAT
     3627           3636
AAA AAA AAA AAA AAA AAA AA 3'
```

FIGURE 1J

```
  1  MLLLG------LCLGLSLCVGSQEEAQSWG         688183
  1  MKRLTC----FFICFFLSEVSGFEIPINGLS         GI 33985
  1  MDGAMGPRGLLCMYLVSL-LILQAMPALG           GI 33989
  1  M--------VALSHL-GSALQLGSLC              GI 288563

26  HSSEQDGL---------RVPRQVRLLQRL-          688183
 28  EFVDYEDLVELAPGKFQLVAENRRYQRSLP          GI 33985
 30  --------SATGRSKSSE----KRQAV             GI 33989
 18  -FPRSPFRLLG----------KRSLP              GI 288563

46  -KTKPLMTE--------FSVKSTIISRYAF          688183
 58  GESEEMMEEVDQVTLYSYKVQSTITSRMAT          GI 33985
 45  DTA-----VDGVFIRSLKVNCKVTSRFAH           GI 33989
 33  EGV----ANGIEVYSTKINSKVTSRFAH            GI 288563

67  TTVSCRMLNRASEDQDIEFQMQIPAAAFIT          688183
 88  TMIQSKVVNNSPQPQNVVFDVQIPKGAFIS          GI 33985
 69  YVVTSQVVNTANEAREVAFDLEIPKTAFIS          GI 33989
 57  NVVTMRAVNRADTAKEVSFDVELPKTAFIT          GI 288563

97  NFTMLIGDKVYQGEITEREKKSGDRVKEKR          688183
118  NFSMTVDGKTFRSSIKEKTVGRALYAQARA          GI 33985
 99  DFAVTADGNAFIGDIKDKVTAWKQYRKAAI          GI 33989
 87  NFTLTIDGVTYPGNVKEKEVAKKQYEKAVS          GI 288563
```

FIGURE 2A

```
127  NKTTEE---NGEKGTEIFRASAVIPSKDKA   688183
148  KGKTAGLVRSSALDMENFRTEVNVLPGAKV   GI 33985
129  SGENAGLVRASGRTMEQFTIHLTVNPQSKV   GI 33989
117  QGKTAGLVKASGRKLEKFTVSVNVAAGSKV   GI 288563

154  AFFLSYEELLQRRLGKYEHSISVRPQQLSG   688183
178  QFELHYQEVKWRKLGSYEHRIYLQPGRLAK   GI 33985
159  TFQLTYEEVLKRNHMQYEIVIKVKPKQLVH   GI 33989
147  TFELTYEELLKRHHKGKYEMYLKVQPKQLVK   GI 288563

184  RLSVDVNILESAGIASLEVLPLHNSRQRGS   688183
208  HLEVDVWVIEPQGLRFLHV-----PDT    GI 33985
189  HFEIDVDDIFEPQGISKLDA-----QAS    GI 33989
177  HFEIEVDIFEPQGISMLDA-----EAS    GI 288563

214  GREDDSGPPPSTVINQNETFANIIFKPTV   688183
230  FEGHFDGVPVISKG-QQK--AHVSFKPTV   GI 33985
211  FLPKELAAQTIKKSFSGKK--GHVLFRPTV   GI 33989
199  FITNDLLGSALTKSFSGKK--GHVSFKPSL   GI 288563

244  VQQ---ARIAQNGILGDFIIRYDVNREQSI   688183
256  AQQRICPSCRETAVDGELVVLYDVKREEKA   GI 33985
239  SQQQSCPTCSTSLLNGHFKVTYDVTRDE-I GI 33989
227  DQQRSCPTCTDSLLNGDFITYDVNRES-P   GI 288563
```

```
421  NNTREAARGQVCIFTIGIGNDVDFRLLEKL      688183
436  KNVKENIQDNISLFSLGMGFDVDYDFLKRL      GI 33985
418  KNVRNAIRGFPLYNLGFHNVDFNFLEVM        GI 33989
406  ENVRNAIGGKFPLYNLFGNNLYNFLENM        GI 288563

451  SLENCGLTRRVHEEEDAGSQLIGFYDEIRT      688183
466  SNENHGIAQRIYGNQDTSSQLKKFYNQVST      GI 33985
448  SMENNGRAQRIYEDHDATQQLQGFYSQVAK      GI 33989
436  ALENHGFARRIYEDSDADLQLQGFYEEVAN      GI 288563

481  PLLSDIRIDYPPSSVVQATKTLFPNYFNGS      688183
496  PLLRNVQFNYPHTSVTDVTQNNEHNYFGGS      GI 33985
478  PLLVDVDLQYPQDAVLALTQNHHKQYYEGS      GI 33989
466  PLLTGVEMEYPENAILDLTQNTYQHFYDGS      GI 288563

511  EIIAGKLVDRKLDHLHVEVTASNSKKFII      688183
526  EIVVAGKFDPAKLDQIESVITATSANTQLV      GI 33985
508  EIVVAGRIADNKQSSFKADVQAHGEGQEFS      GI 33989
496  EIVVAGRLVDEDMNSFKADVKGHGATNDLT      GI 288563

541  LKTDVPVRPQKAGKDVTGSPRPGGDGEGDT      688183
556  LETLAQM------DDLQDFLSKDKHADPD-      GI 33985
538  ITCLVDE------EEMKKLLRERGHMLEN-      GI 33989
526  FTEEVDM------KEMEKALQERDYIFGN-      GI 288563
```

FIGURE 2D

```
571 NHIERLWSYLTTKELLSSWLQSDDEPEKER        688183
579 -FTRKLWAYLTINQLLAERSLAPTAAAKRR        GI 33985
561 -HVERLWAYLTIQELLAKR-MKVDREVRAN        GI 33989
549 -YIERLWAYLTIEQLLEKR-KNAHGEEKEN        GI 288563

601 LRQRAQALAVSYRFLTPFTSMKLRGPVPRM        688183
608 ITRSILQMSLDHHIVTPLTSLVIEN--EAG        GI 33985
589 LSSQALRMSLDYGFVTPLTSMSIRGMADQD        GI 33989
577 LTARALDLSLKYHFVTPLTSMVVTKPEDNE        GI 288563

631 DG--LEEAHGMSAA-------- -MGPEP        688183
636 DERMLADAPPQDPSCCSGALYYGSKVVPDS        GI 33985
619 GLKPTIDKPSEDSP--PL--- -EMLGPRR        GI 33989
607 DERAIADKPGEDAE-------A-TPVSPAM        GI 288563

648 VVQSVRGAGTQPGPLLKKPYQPRIKISKTS        688183
666 TPSWANPSPTPVISMLAQGSQVLESTPPPH        GI 33985
642 TFVLSALQPSPTHS--SSNTQRL-- -PDR        GI 33989
629 SY-LTSYQPPQ----------- ---NP        GI 288563

678 --VDGDPHFVVDFPLSRLTVCFNIDGQPG        688183
696 VMRVENDPHFIIYLPKSQKNICFNIDSEPG        GI 33985
666 VTGVDTDPHFIIHVPQKEDTLCFNINEEPG        GI 33989
641 YYVDGDPHFIIQIPEKDDALCFNIDEAPG        GI 288563
```

| | | | | | | | | | | | | | | | | | | | | | | | | |
|---|---|---|---|---|---|---|---|---|---|---|---|---|---|---|---|---|---|---|---|---|---|---|---|---|
|853|T|E|D|P|A|G|P|S|Q|N|L|T|H|P|L|L|Q|V|G|E|G|P|E|A|V|L|T|V|K|688183|
|872|F|N|E|R|P|G|K|D|P|-|-|-|-|-|-|-|-|-|-|-|-|E|K|P|E|A|S|M|E|V|K|GI 33985|
|843|S|D|I|H|P|G|S|D|P|-|-|-|-|-|-|-|-|-|-|-|-|T|K|P|D|A|T|M|V|R|GI 33989|
|817|S|D|I|R|P|G|S|D|P|-|-|-|-|-|-|-|-|-|-|-|-|T|K|P|D|A|T|L|V|V|K|GI 288563|

| | | | | | | | | | | | | | | | | | | | | | | |
|---|---|---|---|---|---|---|---|---|---|---|---|---|---|---|---|---|---|---|---|---|---|---|
|883|G|H|Q|V|P|V|V|W|K|Q|R|K|I|Y|N|G|E|-|-|-|E|Q|I|D|C|W|F|A|R|688183|
|891|G|Q|K|L|I|T|R|G|L|Q|K|D|Y|R|T|D|L|V|F|G|T|D|V|T|C|W|F|V|H|GI 33985|
|862|N|R|R|L|T|V|T|R|G|L|Q|K|D|Y|S|K|D|P|W|H|G|A|E|V|S|C|W|F|I|H|GI 33989|
|836|N|H|Q|L|I|V|T|R|G|S|Q|K|D|Y|R|K|D|A|S|I|G|T|K|V|V|C|W|F|V|H|GI 288563|

| | | | | | | | | | | | | | | | | | | | | | | |
|---|---|---|---|---|---|---|---|---|---|---|---|---|---|---|---|---|---|---|---|---|---|---|
|909|N|N|A|A|K|L|I|D|G|E|Y|K|D|Y|L|A|S|H|P|F|D|T|G|M|T|L|G|R|G|M|688183|
|921|N|S|G|K|G|F|I|D|G|H|Y|K|D|Y|F|V|P|Q|L|Y|-|-|-|-|-|-|-|S|F|GI 33985|
|892|N|N|G|A|G|L|I|D|G|A|Y|T|D|Y|I|V|P|D|I|F|GI 33989|
|866|N|N|E|G|L|I|D|G|V|H|T|D|Y|I|V|P|N|L|F|GI 288563|

| | | | | |
|---|---|---|---|---|
|939|S|R|E|L|688183|
|943|L|K|R|P|GI 33985|
|911| | | | |GI 33989|
|885| | | | |GI 288563|

FIGURE 2G

SEQUENCE LISTING (1) GENERAL INFORMATION:

(iii) NUMBER OF SEQUENCES: 5

(2) INFORMATION FOR SEQ ID NO: 1:

(i) SEQUENCE CHARACTERISTICS:
      (A) LENGTH: 942 amino acids
      (B) TYPE: amino acid
      (C) STRANDEDNESS: single
      (D) TOPOLOGY: linear (vii) IMMEDIATE SOURCE:
      (A) LIBRARY: UTRSNOT02
      (B) CLONE: 688183

(xi) SEQUENCE DESCRIPTION: SEQ ID NO: 1 :

```
Met Leu Leu Leu Leu Gly Leu Cys Leu Gly Leu Ser Leu Cys Val
                  5                  10                  15

Gly Ser Gln Glu Glu Ala Gln Ser Trp Gly His Ser Ser Glu Gln
                 20                  25                  30

Asp Gly Leu Arg Val Pro Arg Gln Val Arg Leu Leu Gln Arg Leu
                 35                  40                  45

Lys Thr Lys Pro Leu Met Thr Glu Phe Ser Val Lys Ser Thr Ile
                 50                  55                  60

Ile Ser Arg Tyr Ala Phe Thr Thr Val Ser Cys Arg Met Leu Asn
                 65                  70                  75

Arg Ala Ser Glu Asp Gln Asp Ile Glu Phe Gln Met Gln Ile Pro
                 80                  85                  90

Ala Ala Ala Phe Ile Thr Asn Phe Thr Met Leu Ile Gly Asp Lys
                 95                 100                 105

Val Tyr Gln Gly Glu Ile Thr Glu Arg Glu Lys Lys Ser Gly Asp
                110                 115                 120

Arg Val Lys Glu Lys Arg Asn Lys Thr Thr Glu Glu Asn Gly Glu
                125                 130                 135

Lys Gly Thr Glu Ile Phe Arg Ala Ser Ala Val Ile Pro Ser Lys
                140                 145                 150
```

```
Asp Lys Ala Ala Phe Phe Leu Ser Tyr Glu Glu Leu Leu Gln Arg
            155                 160                 165

Arg Leu Gly Lys Tyr Glu His Ser Ile Ser Val Arg Pro Gln Gln
            170                 175                 180

Leu Ser Gly Arg Leu Ser Val Asp Val Asn Ile Leu Glu Ser Ala
            185                 190                 195

Gly Ile Ala Ser Leu Glu Val Leu Pro Leu His Asn Ser Arg Gln
            200                 205                 210

Arg Gly Ser Gly Arg Gly Glu Asp Asp Ser Gly Pro Pro Ser
            215                 220                 225

Thr Val Ile Asn Gln Asn Glu Thr Phe Ala Asn Ile Ile Phe Lys
            230                 235                 240

Pro Thr Val Val Gln Gln Ala Arg Ile Ala Gln Asn Gly Ile Leu
            245                 250                 255

Gly Asp Phe Ile Ile Arg Tyr Asp Val Asn Arg Glu Gln Ser Ile
            260                 265                 270

Gly Asp Ile Gln Val Leu Asn Gly Tyr Phe Val His Tyr Phe Ala
            275                 280                 285

Pro Lys Asp Leu Pro Pro Leu Pro Lys Asn Val Val Phe Val Leu
            290                 295                 300

Asp Ser Ser Ala Ser Met Val Gly Thr Lys Leu Arg Gln Thr Lys
            305                 310                 315

Asp Ala Leu Phe Thr Ile Leu His Asp Leu Arg Pro Gln Asp Arg
            320                 325                 330

Phe Ser Ile Ile Gly Phe Ser Asn Arg Ile Lys Val Trp Lys Asp
            335                 340                 345

His Leu Ile Ser Val Thr Pro Asp Ser Ile Arg Asp Gly Lys Val
            350                 355                 360

Tyr Ile His His Met Ser Pro Thr Gly Gly Thr Asp Ile Asn Gly
            365                 370                 375

Ala Leu Gln Arg Ala Ile Arg Leu Leu Asn Lys Tyr Val Ala His
            380                 385                 390

Ser Gly Ile Gly Asp Arg Ser Val Ser Leu Ile Val Phe Leu Thr
            395                 400                 405

Asp Gly Lys Pro Thr Val Gly Glu Thr His Thr Leu Lys Ile Leu
            410                 415                 420

Asn Asn Thr Arg Glu Ala Ala Arg Gly Gln Val Cys Ile Phe Thr
            425                 430                 435

Ile Gly Ile Gly Asn Asp Val Asp Phe Arg Leu Leu Glu Lys Leu
            440                 445                 450

Ser Leu Glu Asn Cys Gly Leu Thr Arg Arg Val His Glu Glu Glu
            455                 460                 465

Asp Ala Gly Ser Gln Leu Ile Gly Phe Tyr Asp Glu Ile Arg Thr
            470                 475                 480

Pro Leu Leu Ser Asp Ile Arg Ile Asp Tyr Pro Pro Ser Ser Val
            485                 490                 495

Val Gln Ala Thr Lys Thr Leu Phe Pro Asn Tyr Phe Asn Gly Ser
            500                 505                 510

Glu Ile Ile Ile Ala Gly Lys Leu Val Asp Arg Lys Leu Asp His
            515                 520                 525

Leu His Val Glu Val Thr Ala Ser Asn Ser Lys Lys Phe Ile Ile
            530                 535                 540
```

-continued

```
Leu Lys Thr Asp Val Pro Val Arg Pro Gln Lys Ala Gly Lys Asp
            545                 550                 555
Val Thr Gly Ser Pro Arg Pro Gly Gly Asp Gly Glu Gly Asp Thr
            560                 565                 570
Asn His Ile Glu Arg Leu Trp Ser Tyr Leu Thr Thr Lys Glu Leu
            575                 580                 585
Leu Ser Ser Trp Leu Gln Ser Asp Asp Glu Pro Glu Lys Glu Arg
            590                 595                 600
Leu Arg Gln Arg Ala Gln Ala Leu Ala Val Ser Tyr Arg Phe Leu
            605                 610                 615
Thr Pro Phe Thr Ser Met Lys Leu Arg Gly Pro Val Pro Arg Met
            620                 625                 630
Asp Gly Leu Glu Glu Ala His Gly Met Ser Ala Ala Met Gly Pro
            635                 640                 645
Glu Pro Val Val Gln Ser Val Arg Gly Ala Gly Thr Gln Pro Gly
            650                 655                 660
Pro Leu Leu Lys Lys Pro Tyr Gln Pro Arg Ile Lys Ile Ser Lys
            665                 670                 675
Thr Ser Val Asp Gly Asp Pro His Phe Val Val Asp Phe Pro Leu
            680                 685                 690
Ser Arg Leu Thr Val Cys Phe Asn Ile Asp Gly Gln Pro Gly Asp
            695                 700                 705
Ile Leu Arg Leu Val Ser Asp His Arg Asp Ser Gly Val Thr Val
            710                 715                 720
Asn Gly Glu Leu Ile Gly Ala Pro Ala Pro Pro Asn Gly His Lys
            725                 730                 735
Lys Gln Arg Thr Tyr Leu Arg Thr Ile Thr Ile Leu Ile Asn Lys
            740                 745                 750
Pro Glu Arg Ser Tyr Leu Glu Ile Thr Pro Ser Arg Val Ile Leu
            755                 760                 765
Asp Gly Gly Asp Arg Leu Val Leu Pro Cys Asn Gln Ser Val Val
            770                 775                 780
Val Gly Ser Trp Gly Leu Glu Val Ser Val Ser Ala Asn Ala Asn
            785                 790                 795
Val Thr Val Thr Ile Gln Gly Ser Ile Ala Phe Val Ile Leu Ile
            800                 805                 810
His Leu Tyr Lys Lys Pro Ala Pro Phe Gln Arg His His Leu Gly
            815                 820                 825
Phe Tyr Ile Ala Asn Ser Glu Gly Leu Ser Ser Asn Cys His Gly
            830                 835                 840
Leu Leu Gly Gln Phe Leu Asn Gln Asp Ala Arg Leu Thr Glu Asp
            845                 850                 855
Pro Ala Gly Pro Ser Gln Asn Leu Thr His Pro Leu Leu Leu Gln
            860                 865                 870
Val Gly Glu Gly Pro Glu Ala Val Leu Thr Val Lys Gly His Gln
            875                 880                 885
Val Pro Val Val Trp Lys Gln Arg Lys Ile Tyr Asn Gly Glu Glu
            890                 895                 900
Gln Ile Asp Cys Trp Phe Ala Arg Asn Asn Ala Ala Lys Leu Ile
            905                 910                 915
Asp Gly Glu Tyr Lys Asp Tyr Leu Ala Ser His Pro Phe Asp Thr
            920                 925                 930
```

```
Gly Met Thr Leu Gly Arg Gly Met Ser Arg Glu Leu
            935                 940
```

(2) INFORMATION FOR SEQ ID NO: 2:

(i) SEQUENCE CHARACTERISTICS:
        (A) LENGTH: 3636 base pairs
        (B) TYPE: nucleic acid
        (C) STRANDEDNESS: single
        (D) TOPOLOGY: linear (vii) IMMEDIATE SOURCE:
        (A) LIBRARY: UTRSNOT02
        (B) CLONE: 688183

(xi) SEQUENCE DESCRIPTION: SEQ ID NO: 2 :

```
CCCTGAGAGC GTCCCGCAGT GGCTGGAGCC CTGGGCGCTG CAAACGTGTC CCGCCGGGTC     60

CCCGAGCGTC CCGCGCCCTC GCCCCGCCAT GCTCCTGCTG CTGGGGCTGT GCCTGGGGCT    120

GTCCCTGTGT GTGGGGTCGC AGGAAGAGGC GCAGAGCTGG GGCCACTCTT CGGAGCAGGA    180

TGGACTCAGG GTCCCGAGGC AAGTCAGACT GTTGCAGAGG CTGAAAACCA AACCTTTGAT    240

GACAGAATTC TCAGTGAAGT CTACCATCAT TTCCCGTTAT GCCTTCACTA CGGTTTCCTG    300

CAGAATGCTG AACAGAGCTT CTGAAGACCA GGACATTGAG TTCCAGATGC AGATTCCAGC    360

TGCAGCTTTC ATCACCAACT TCACTATGCT TATTGGAGAC AAGGTGTATC AGGGCGAAAT    420

TACAGAGAGA GAAAGAAGA GTGGTGATAG GGTAAAAGAG AAAAGGAATA AACCACAGA      480

AGAAAATGGA GAGAAGGGGA CTGAAATATT CAGAGCTTCT GCAGTGATTC CCAGCAAGGA    540

CAAAGCCGCC TTTTTCCTGA GTTATGAGGA GCTTCTGCAG AGGCGCCTGG GCAAGTACGA    600

GCACAGCATC AGCGTGCGGC CCCAGCAGCT GTCCGGGAGG CTGAGCGTGG ACGTGAATAT    660

CCTGGAGAGC GCGGGCATCG CATCCCTGGA GGTGCTGCCG CTTCACAACA GCAGGCAGAG    720

GGGCAGTGGG CGCGGGGAAG ATGATTCTGG GCCTCCCCCA TCTACTGTCA TTAACCAAAA    780

TGAAACATTT GCCAACATAA TTTTTAAACC TACTGTAGTA CAACAAGCCA GGATTGCCCA    840

GAATGGAATT TTGGGAGACT TTATCATTAG ATATGACGTC AATAGAGAAC AGAGCATTGG    900

GGACATCCAG GTTCTAAATG CTATTTTGT GCACTACTTT GCTCCTAAAG ACCTTCCTCC     960

TTTACCCAAG AATGTGGTAT TCGTGCTTGA CAGCAGTGCT TCTATGGTGG GAACCAAACT   1020

CCGGCAGACC AAGGATGCCC TCTTCACAAT TCTCCATGAC CTCCGACCCC AGGACCGTTT   1080

CAGTATCATT GGATTTTCCA ACCGGATCAA AGTATGGAAG GACCACTTGA TATCAGTCAC   1140

TCCAGACAGC ATCAGGGATG GAAAGTGTA CATTCACCAT ATGTCACCCA CTGGAGGCAC    1200

AGACATCAAC GGGGCCCTGC AGAGGGCCAT CAGGCTCCTC AACAAGTACG TGGCCCACAG   1260

TGGCATTGGA GACCGGAGCG TGTCCCTCAT CGTCTTCCTG ACGGATGGGA AGCCCACGGT   1320

CGGGGAGACG CACACCCTCA AGATCCTCAA CAACACCCGA GAGGCCGCCC GAGGCCAAGT   1380

CTGCATCTTC ACCATTGGCA TCGGCAACGA CGTGGACTTC AGGCTGCTGG AGAAACTGTC   1440

GCTGGAGAAC TGTGGCCTCA CACGGCGCGT GCACGAGGAG GAGGACGCAG GCTCGCAGCT   1500

CATCGGGTTC TACGATGAAA TCAGGACCCC GCTCCTCTCT GACATCCGCA TCGATTATCC   1560

CCCCAGCTCA GTGGTGCAGG CCACCAAGAC CCTGTTCCCC AACTACTTCA ACGGCTCGGA   1620

GATCATCATT GCGGGGAAGC TGGTGGACAG GAAGCTGGAT CACCTGCACG TGGAGGTCAC   1680

CGCCAGCAAC AGTAAGAAAT TCATCATCCT GAAGACAGAT GTGCCTGTGC GGCCTCAGAA   1740

GGCAGGGAAA GATGTCACAG GAAGCCCCAG GCCTGGAGGC GATGGAGAGG GGGACACCAA   1800

CCACATCGAG CGTCTCTGGA GCTACCTCAC CACAAAGGAG CTGCTGAGCT CCTGGCTGCA   1860
```

```
AAGTGACGAT GAACCGGAGA AGGAGCGGCT GCGGCAGCGG GCCCAGGCCC TGGCTGTGAG      1920

CTACCGCTTC CTCACTCCCT TCACCTCCAT GAAGCTGAGG GGGCCGGTCC CACGCATGGA      1980

TGGCCTGGAG GAGGCCCACG GCATGTCGGC TGCCATGGGA CCCGAACCGG TGGTGCAGAG      2040

CGTGCGAGGA GCTGGCACGC AGCCAGGGCC TTTGCTCAAG AAGCCATACC AGCCAAGAAT      2100

TAAAATCTCT AAAACATCAG TGGATGGTGA TCCCCACTTT GTTGTGGATT TCCCCCTGAG      2160

CAGACTCACC GTGTGCTTCA ACATTGATGG GCAGCCCGGG GACATCCTCA GGCTGGTCTC      2220

TGATCACAGG GACTCTGGTG TCACAGTGAA CGGAGAGTTA ATTGGGGCAC CCGCCCCTCC      2280

AAATGGCCAC AAGAAACAGC GCACTTACTT GCGCACTATC ACCATCCTCA TCAACAAGCC      2340

AGAGAGATCT TATCTCGAGA TCACACCGAG CAGAGTCATC TTGGATGGTG GGACAGACT       2400

GGTGCTCCCC TGCAACCAGA GTGTGGTGGT GGGGAGCTGG GGGCTGGAGG TGTCCGTGTC      2460

TGCCAACGCC AATGTCACCG TCACCATCCA GGGCTCCATA GCCTTTGTCA TCCTCATCCA      2520

CCTCTACAAA AAGCCGGCGC CCTTCCAGCG ACACCACCTG GGTTTCTACA TTGCCAACAG      2580

CGAGGGCCTT TCCAGCAACT GCCACGGACT GCTGGGTCAG TTCCTGAATC AGGATGCCAG      2640

ACTCACAGAA GACCCTGCAG GGCCCAGCCA GAACCTCACT CACCCTCTGC TCCTTCAGGT      2700

GGGAGAGGGG CCTGAGGCCG TCCTAACAGT GAAAGGCCAC CAAGTCCCAG TGGTCTGGAA      2760

GCAAAGGAAG ATTTACAACG GGGAAGAGCA GATAGACTGC TGGTTTGCCA GGAACAATGC      2820

CGCCAAACTG ATTGACGGGG AGTACAAGGA TTACCTGGCA TCCCATCCAT TTGACACAGG      2880

GATGACACTT GGCCGGGGAA TGTCCAGGGA GCTCTGAAGC TGGCAGCCTT AAAGATGCAA      2940

GTGCATGAAG GACAGTGATG TGGGGAGGCC GTGGGGCAGC TCTTTTCATG GCTTGTACAC      3000

GCCTCAGCTC CTGGCAATTA GCTGGACTCC ATGACCCACC CCTGGTGCAG CATAGATCCG      3060

ACGTCTGTCT GGGCGAAGGG TAGGGGTGGG TAGGGGCGGG AAGCCTGAGT GCAAATGTCA      3120

TTTCCCTCTA CTGCCTCTTC CTGCCTCTCC CCACCCTGCC CACATCCACA GAGGGGAGAG      3180

AAGGGTCATA GCTAAATGCA ACAAAGTCTG TATCTTGTCC CAACCTGCTT TTCTGTTCTG      3240

TTAGCATATC ATAAAGTAAG CCTTTCTGGT GAAGGAAGGT TGCTATGAAA CTTTTTTTC      3300

TGGTGGAAAT GGCCAAGTTT AGGCACTCTG CTTTTTGCCT TACACTAATG CTTAGAAAGC      3300

TGTCTTTTCA GTGGTGTTGC AGCCCCCAGA TGTGTGGCCA ACCTCTGCTG CAAAGGAATC      3420

TCTTGCTGAG TCCAGGCCAC CAATCAGGCA AATAGCCCAT ACATTTGATC GTTGTAAACC      3480

ATGAAGTCTT TTCTTGCAAG ACGTTTTTCT TCTGCTGTGG TATCTTGCCC TTAAAAATTA      3540

GTTTTCATTA AAAAGAAATT TGATTGAAAA TTAAAAAAAA ATAAAAAAAA AAGAAAAAAA      3600

AAAAGAAAGA AAAAATAAAA AAAAAAAAAA AAAAAA                                3636
```

(2) INFORMATION FOR SEQ ID NO: 3:

(i) SEQUENCE CHARACTERISTICS:
        (A) LENGTH: 946 amino acids
        (B) TYPE: amino acid
        (C) STRANDEDNESS: single
        (D) TOPOLOGY: linear (vii) IMMEDIATE SOURCE:
        (A) LIBRARY: GENEBANK
        (B) CLONE: gi33985

(xi) SEQUENCE DESCRIPTION: SEQ ID NO: 3 :

Met Lys Arg Leu Thr Cys Phe Phe Ile Cys Phe Phe Leu Ser Glu
             5               10             15

-continued

```
Val Ser Gly Phe Glu Ile Pro Ile Asn Gly Leu Ser Glu Phe Val
             20                  25                  30

Asp Tyr Glu Asp Leu Val Glu Leu Ala Pro Gly Lys Phe Gln Leu
             35                  40                  45

Val Ala Glu Asn Arg Arg Tyr Gln Arg Ser Leu Pro Gly Glu Ser
             50                  55                  60

Glu Glu Met Met Glu Glu Val Asp Gln Val Thr Leu Tyr Ser Tyr
             65                  70                  75

Lys Val Gln Ser Thr Ile Thr Ser Arg Met Ala Thr Thr Met Ile
             80                  85                  90

Gln Ser Lys Val Val Asn Asn Ser Pro Gln Pro Gln Asn Val Val
             95                 100                 105

Phe Asp Val Gln Ile Pro Lys Gly Ala Phe Ile Ser Asn Phe Ser
            110                 115                 120

Met Thr Val Asp Gly Lys Thr Phe Arg Ser Ser Ile Lys Glu Lys
            125                 130                 135

Thr Val Gly Arg Ala Leu Tyr Ala Gln Ala Arg Ala Lys Gly Lys
            140                 145                 150

Thr Ala Gly Leu Val Arg Ser Ser Ala Leu Asp Met Glu Asn Phe
            155                 160                 165

Arg Thr Glu Val Asn Val Leu Pro Gly Ala Lys Val Gln Phe Glu
            170                 175                 180

Leu His Tyr Gln Glu Val Lys Trp Arg Lys Leu Gly Ser Tyr Glu
            185                 190                 195

His Arg Ile Tyr Leu Gln Pro Gly Arg Leu Ala Lys His Leu Glu
            200                 205                 210

Val Asp Val Trp Val Ile Glu Pro Gln Gly Leu Arg Phe Leu His
            215                 220                 225

Val Pro Asp Thr Phe Glu Gly His Phe Asp Gly Val Pro Val Ile
            230                 235                 240

Ser Lys Gly Gln Gln Lys Ala His Val Ser Phe Lys Pro Thr Val
            245                 250                 255

Ala Gln Gln Arg Ile Cys Pro Ser Cys Arg Glu Thr Ala Val Asp
            260                 265                 270

Gly Glu Leu Val Val Leu Tyr Asp Val Lys Arg Glu Glu Lys Ala
            275                 280                 285

Gly Glu Leu Glu Val Phe Asn Gly Tyr Phe Val His Phe Phe Ala
            290                 295                 300

Pro Asp Asn Leu Asp Pro Ile Pro Lys Asn Ile Leu Phe Val Ile
            305                 310                 315

Asp Val Ser Gly Ser Met Trp Gly Val Lys Met Lys Gln Thr Val
            320                 325                 330

Glu Ala Met Lys Thr Ile Leu Asp Asp Leu Arg Ala Glu Asp His
            335                 340                 345

Phe Ser Val Ile Asp Phe Asn Gln Asn Ile Arg Thr Trp Arg Asn
            350                 355                 360

Asp Leu Phe Gln Leu Gln Lys His Arg Leu Gln Ile Ala Lys Arg
            365                 370                 375

Tyr Ile Glu Lys Ile Gln Pro Ser Gly Gly Thr Asn Ile Asn Glu
            380                 385                 390

Ala Leu Leu Arg Ala Ile Phe Ile Leu Asn Glu Ala Asn Asn Leu
            395                 400                 405
```

-continued

Gly Leu Leu Asp Pro Asn Ser Val Ser Leu Ile Ile Leu Val Ser
            410                 415                 420

Asp Gly Asp Pro Thr Val Gly Glu Leu Lys Leu Ser Lys Ile Gln
            425                 430                 435

Lys Asn Val Lys Glu Asn Ile Gln Asp Asn Ile Ser Leu Phe Ser
            440                 445                 450

Leu Gly Met Gly Phe Asp Val Asp Tyr Asp Phe Leu Lys Arg Leu
            455                 460                 465

Ser Asn Glu Asn His Gly Ile Ala Gln Arg Ile Tyr Gly Asn Gln
            470                 475                 480

Asp Thr Ser Ser Gln Leu Lys Lys Phe Tyr Asn Gln Val Ser Thr
            485                 490                 495

Pro Leu Leu Arg Asn Val Gln Phe Asn Tyr Pro His Thr Ser Val
            500                 505                 510

Thr Asp Val Thr Gln Asn Asn Phe His Asn Tyr Phe Gly Gly Ser
            515                 520                 525

Glu Ile Val Val Ala Gly Lys Phe Asp Pro Ala Lys Leu Asp Gln
            530                 535                 540

Ile Glu Ser Val Ile Thr Ala Thr Ser Ala Asn Thr Gln Leu Val
            545                 550                 555

Leu Glu Thr Leu Ala Gln Met Asp Asp Leu Gln Asp Phe Leu Ser
            560                 565                 570

Lys Asp Lys His Ala Asp Pro Asp Phe Thr Arg Lys Leu Trp Ala
            575                 580                 585

Tyr Leu Thr Ile Asn Gln Leu Leu Ala Glu Arg Ser Leu Ala Pro
            590                 595                 600

Thr Ala Ala Ala Lys Arg Arg Ile Thr Arg Ser Ile Leu Gln Met
            605                 610                 615

Ser Leu Asp His His Ile Val Thr Pro Leu Thr Ser Leu Val Ile
            620                 625                 630

Glu Asn Glu Ala Gly Asp Glu Arg Met Leu Ala Asp Ala Pro Pro
            635                 640                 645

Gln Asp Pro Ser Cys Cys Ser Gly Ala Leu Tyr Tyr Gly Ser Lys
            650                 655                 660

Val Val Pro Asp Ser Thr Pro Ser Trp Ala Asn Pro Ser Pro Thr
            665                 670                 675

Pro Val Ile Ser Met Leu Ala Gln Gly Ser Gln Val Leu Glu Ser
            680                 685                 690

Thr Pro Pro Pro His Val Met Arg Val Glu Asn Asp Pro His Phe
            695                 700                 705

Ile Ile Tyr Leu Pro Lys Ser Gln Lys Asn Ile Cys Phe Asn Ile
            710                 715                 720

Asp Ser Glu Pro Gly Lys Ile Leu Asn Leu Val Ser Asp Pro Glu
            725                 730                 735

Ser Gly Ile Val Val Asn Gly Gln Leu Val Gly Ala Lys Lys Pro
            740                 745                 750

Asn Asn Gly Lys Leu Ser Thr Tyr Phe Gly Lys Leu Gly Phe Tyr
            755                 760                 765

Phe Gln Ser Glu Asp Ile Lys Ile Glu Ile Ser Thr Glu Thr Ile
            770                 775                 780

Thr Leu Ser His Gly Ser Ser Thr Phe Ser Leu Ser Trp Ser Asp
            785                 790                 795

-continued

```
Thr Ala Gln Val Thr Asn Gln Arg Val Gln Ile Ser Val Lys Lys
                800                 805                 810

Glu Lys Val Val Thr Ile Thr Leu Asp Lys Glu Met Ser Phe Ser
                815                 820                 825

Val Leu Leu His Arg Val Trp Lys Lys His Pro Val Asn Val Asp
                830                 835                 840

Phe Leu Gly Ile Tyr Ile Pro Pro Thr Asn Lys Phe Ser Pro Lys
                845                 850                 855

Ala His Gly Leu Ile Gly Gln Phe Met Gln Glu Pro Lys Ile His
                860                 865                 870

Ile Phe Asn Glu Arg Pro Gly Lys Asp Pro Glu Lys Pro Glu Ala
                875                 880                 885

Ser Met Glu Val Lys Gly Gln Lys Leu Ile Ile Thr Arg Gly Leu
                890                 895                 900

Gln Lys Asp Tyr Arg Thr Asp Leu Val Phe Gly Thr Asp Val Thr
                905                 910                 915

Cys Trp Phe Val His Asn Ser Gly Lys Gly Phe Ile Asp Gly His
                920                 925                 930

Tyr Lys Asp Tyr Phe Val Pro Gln Leu Tyr Ser Phe Leu Lys Arg
                935                 940                 945

Pro
```

(2) INFORMATION FOR SEQ ID NO: 4:

(i) SEQUENCE CHARACTERISTICS:
        (A) LENGTH: 911 amino acids
        (B) TYPE: amino acid
        (C) STRANDEDNESS: single
        (D) TOPOLOGY: linear (vii) IMMEDIATE SOURCE:
        (A) LIBRARY: GENEBABK
        (B) CLONE: gi33989

(xi) SEQUENCE DESCRIPTION: SEQ ID NO: 4 :

```
Met Asp Gly Ala Met Gly Pro Arg Gly Leu Leu Leu Cys Met Tyr
                5                   10                  15

Leu Val Ser Leu Leu Ile Leu Gln Ala Met Pro Ala Leu Gly Ser
                20                  25                  30

Ala Thr Gly Arg Ser Lys Ser Ser Glu Lys Arg Gln Ala Val Asp
                35                  40                  45

Thr Ala Val Asp Gly Val Phe Ile Arg Ser Leu Lys Val Asn Cys
                50                  55                  60

Lys Val Thr Ser Arg Phe Ala His Tyr Val Val Thr Ser Gln Val
                65                  70                  75

Val Asn Thr Ala Asn Glu Ala Arg Glu Val Ala Phe Asp Leu Glu
                80                  85                  90

Ile Pro Lys Thr Ala Phe Ile Ser Asp Phe Ala Val Thr Ala Asp
                95                  100                 105

Gly Asn Ala Phe Ile Gly Asp Ile Lys Asp Lys Val Thr Ala Trp
                110                 115                 120

Lys Gln Tyr Arg Lys Ala Ala Ile Ser Gly Glu Asn Ala Gly Leu
                125                 130                 135

Val Arg Ala Ser Gly Arg Thr Met Glu Gln Phe Thr Ile His Leu
                140                 145                 150

Thr Val Asn Pro Gln Ser Lys Val Thr Phe Gln Leu Thr Tyr Glu
                155                 160                 165
```

-continued

```
Glu Val Leu Lys Arg Asn His Met Gln Tyr Glu Ile Val Ile Lys
                170                 175                 180

Val Lys Pro Lys Gln Leu Val His His Phe Glu Ile Asp Val Asp
            185                 190                 195

Ile Phe Glu Pro Gln Gly Ile Ser Lys Leu Asp Ala Gln Ala Ser
        200                 205                 210

Phe Leu Pro Lys Glu Leu Ala Ala Gln Thr Ile Lys Lys Ser Phe
    215                 220                 225

Ser Gly Lys Lys Gly His Val Leu Phe Arg Pro Thr Val Ser Gln
230                 235                 240

Gln Gln Ser Cys Pro Thr Cys Ser Thr Ser Leu Leu Asn Gly His
            245                 250                 255

Phe Lys Val Thr Tyr Asp Val Thr Arg Asp Glu Ile Cys Asp Leu
        260                 265                 270

Leu Val Ala Asn Asn His Phe Ala His Phe Phe Ala Pro Gln Asn
    275                 280                 285

Leu Thr Asn Met Asn Lys Asn Val Val Phe Val Ile Asp Ile Ser
290                 295                 300

Gly Ser Met Arg Gly Gln Lys Val Lys Gln Thr Lys Glu Ala Leu
            305                 310                 315

Leu Lys Ile Leu Gly Asp Met Gln Pro Gly Asp Tyr Phe Asp Leu
        320                 325                 330

Val Leu Phe Gly Thr Arg Val Gln Ser Trp Lys Gly Ser Leu Val
    335                 340                 345

Gln Ala Ser Glu Ala Asn Leu Gln Ala Ala Gln Asp Phe Val Arg
350                 355                 360

Gly Phe Ser Leu Asp Glu Ala Thr Asn Leu Asn Gly Gly Leu Leu
            365                 370                 375

Arg Gly Ile Glu Ile Leu Asn Gln Val Gln Glu Ser Leu Pro Glu
        380                 385                 390

Leu Ser Asn His Ala Ser Ile Leu Ile Met Leu Thr Asp Gly Asp
    395                 400                 405

Pro Thr Glu Gly Val Thr Asp Arg Ser Gln Ile Leu Lys Asn Val
410                 415                 420

Arg Asn Ala Ile Arg Gly Arg Phe Pro Leu Tyr Asn Leu Gly Phe
            425                 430                 435

Gly His Asn Val Asp Phe Asn Phe Leu Glu Val Met Ser Met Glu
        440                 445                 450

Asn Asn Gly Arg Ala Gln Arg Ile Tyr Glu Asp His Asp Ala Thr
    455                 460                 465

Gln Gln Leu Gln Gly Phe Tyr Ser Gln Val Ala Lys Pro Leu Leu
470                 475                 480

Val Asp Val Asp Leu Gln Tyr Pro Gln Asp Ala Val Leu Ala Leu
            485                 490                 495

Thr Gln Asn His His Lys Gln Tyr Tyr Glu Gly Ser Glu Ile Val
        500                 505                 510

Val Ala Gly Arg Ile Ala Asp Asn Lys Gln Ser Ser Phe Lys Ala
    515                 520                 525

Asp Val Gln Ala His Gly Glu Gly Gln Glu Phe Ser Ile Thr Cys
530                 535                 540

Leu Val Asp Glu Glu Glu Met Lys Lys Leu Leu Arg Glu Arg Gly
            545                 550                 555
```

-continued

```
His Met Leu Glu Asn His Val Glu Arg Leu Trp Ala Tyr Leu Thr
                560                 565                 570

Ile Gln Glu Leu Leu Ala Lys Arg Met Lys Val Asp Arg Glu Val
                575                 580                 585

Arg Ala Asn Leu Ser Ser Gln Ala Leu Arg Met Ser Leu Asp Tyr
                590                 595                 600

Gly Phe Val Thr Pro Leu Thr Ser Met Ser Ile Arg Gly Met Ala
                605                 610                 615

Asp Gln Asp Gly Leu Lys Pro Thr Ile Asp Lys Pro Ser Glu Asp
                620                 625                 630

Ser Pro Pro Leu Glu Met Leu Gly Pro Arg Arg Thr Phe Val Leu
                635                 640                 645

Ser Ala Leu Gln Pro Ser Pro Thr His Ser Ser Ser Asn Thr Gln
                650                 655                 660

Arg Leu Pro Asp Arg Val Thr Gly Val Asp Thr Asp Pro His Phe
                665                 670                 675

Ile Ile His Val Pro Gln Lys Glu Asp Thr Leu Cys Phe Asn Ile
                680                 685                 690

Asn Glu Glu Pro Gly Val Ile Leu Ser Leu Val Gln Asp Pro Asn
                695                 700                 705

Thr Gly Phe Ser Val Asn Gly Gln Leu Ile Gly Asn Lys Ala Arg
                710                 715                 720

Ser Pro Gly Gln His Asp Gly Thr Tyr Phe Gly Arg Leu Gly Ile
                725                 730                 735

Ala Asn Pro Ala Thr Asp Phe Gln Leu Glu Val Thr Pro Gln Asn
                740                 745                 750

Ile Thr Leu Asn Pro Gly Phe Gly Gly Pro Val Phe Ser Trp Arg
                755                 760                 765

Asp Gln Ala Val Leu Arg Gln Asp Gly Val Val Thr Ile Asn
                770                 775                 780

Lys Lys Arg Asn Leu Val Val Ser Val Asp Asp Gly Thr Phe
                785                 790                 795

Glu Val Val Leu His Arg Val Trp Lys Gly Ser Ser Val His Gln
                800                 805                 810

Asp Phe Leu Gly Phe Tyr Val Leu Asp Ser His Arg Met Ser Ala
                815                 820                 825

Arg Thr His Gly Leu Leu Gly Gln Phe Phe His Pro Ile Gly Phe
                830                 835                 840

Glu Val Ser Asp Ile His Pro Gly Ser Asp Pro Thr Lys Pro Asp
                845                 850                 855

Ala Thr Met Val Val Arg Asn Arg Arg Leu Thr Val Thr Arg Gly
                860                 865                 870

Leu Gln Lys Asp Tyr Ser Lys Asp Pro Trp His Gly Ala Glu Val
                875                 880                 885

Ser Cys Trp Phe Ile His Asn Asn Gly Ala Gly Leu Ile Asp Gly
                890                 895                 900

Ala Tyr Thr Asp Tyr Ile Val Pro Asp Ile Phe
                905                 910
```

(2) INFORMATION FOR SEQ ID NO: 5:

(i) SEQUENCE CHARACTERISTICS:
        (A) LENGTH: 885 amino acids
        (B) TYPE: amino acid (C) STRANDEDNESS: single
        (D) TOPOLOGY: linear (vii) IMMEDIATE SOURCE:
        (A) LIBRARY: GENEBANK
        (B) CLONE: gi288563

(xi) SEQUENCE DESCRIPTION: SEQ ID NO: 5:

Met Val Ala Leu Ser His Leu Gly Ser Ala Leu Gln Leu Gly Ser
                 5                  10                  15

Leu Cys Phe Pro Arg Ser Pro Phe Arg Leu Leu Gly Lys Arg Ser
                20                  25                  30

Leu Pro Glu Gly Val Ala Asn Gly Ile Glu Val Tyr Ser Thr Lys
                35                  40                  45

Ile Asn Ser Lys Val Thr Ser Arg Phe Ala His Asn Val Val Thr
                50                  55                  60

Met Arg Ala Val Asn Arg Ala Asp Thr Ala Lys Glu Val Ser Phe
                65                  70                  75

Asp Val Glu Leu Pro Lys Thr Ala Phe Ile Thr Asn Phe Thr Leu
                80                  85                  90

Thr Ile Asp Gly Val Thr Tyr Pro Gly Asn Val Lys Glu Lys Glu
                95                 100                 105

Val Ala Lys Lys Gln Tyr Glu Lys Ala Val Ser Gln Gly Lys Thr
               110                 115                 120

Ala Gly Leu Val Lys Ala Ser Gly Arg Lys Leu Glu Lys Phe Thr
               125                 130                 135

Val Ser Val Asn Val Ala Ala Gly Ser Lys Val Thr Phe Glu Leu
               140                 145                 150

Thr Tyr Glu Glu Leu Leu Lys Arg His Lys Gly Lys Tyr Glu Met
               155                 160                 165

Tyr Leu Lys Val Gln Pro Lys Gln Leu Val Lys His Phe Glu Ile
               170                 175                 180

Glu Val Asp Ile Phe Glu Pro Gln Gly Ile Ser Met Leu Asp Ala
               185                 190                 195

Glu Ala Ser Phe Ile Thr Asn Asp Leu Leu Gly Ser Ala Leu Thr
               200                 205                 210

Lys Ser Phe Ser Gly Lys Lys Gly His Val Ser Phe Lys Pro Ser
               215                 220                 225

Leu Asp Gln Gln Arg Ser Cys Pro Thr Cys Thr Asp Ser Leu Leu
               230                 235                 240

Asn Gly Asp Phe Thr Ile Thr Tyr Asp Val Asn Arg Glu Ser Pro
               245                 250                 255

Gly Asn Val Gln Ile Val Asn Gly Tyr Phe Val His Phe Phe Ala
               260                 265                 270

Pro Gln Gly Leu Pro Val Val Pro Lys Asn Val Ala Phe Val Ile
               275                 280                 285

Asp Ile Ser Gly Ser Met Ala Gly Arg Lys Leu Glu Gln Thr Lys
               290                 295                 300

Glu Ala Leu Leu Arg Ile Leu Glu Asp Met Lys Glu Glu Asp Tyr
               305                 310                 315

Leu Asn Phe Ile Leu Phe Ser Gly Asp Val Ser Thr Trp Lys Glu
               320                 325                 330

His Leu Val Gln Ala Thr Pro Glu Asn Leu Gln Glu Ala Arg Thr
               335                 340                 345

-continued

```
Phe Val Lys Ser Met Glu Asp Lys Gly Met Thr Asn Ile Asn Asp
                350                 355                 360

Gly Leu Leu Arg Gly Ile Ser Met Leu Asn Lys Ala Arg Glu Glu
            365                 370                 375

His Arg Ile Pro Glu Arg Ser Thr Ser Ile Val Ile Met Leu Thr
            380                 385                 390

Asp Gly Asp Ala Asn Val Gly Glu Ser Arg Pro Glu Lys Ile Gln
            395                 400                 405

Glu Asn Val Arg Asn Ala Ile Gly Gly Lys Phe Pro Leu Tyr Asn
            410                 415                 420

Leu Gly Phe Gly Asn Asn Leu Asn Tyr Asn Phe Leu Glu Asn Met
            425                 430                 435

Ala Leu Glu Asn His Gly Phe Ala Arg Arg Ile Tyr Glu Asp Ser
            440                 445                 450

Asp Ala Asp Leu Gln Leu Gln Gly Phe Tyr Glu Glu Val Ala Asn
            455                 460                 465

Pro Leu Leu Thr Gly Val Glu Met Glu Tyr Pro Glu Asn Ala Ile
            470                 475                 480

Leu Asp Leu Thr Gln Asn Thr Tyr Gln His Phe Tyr Asp Gly Ser
            485                 490                 495

Glu Ile Val Val Ala Gly Arg Leu Val Asp Glu Asp Met Asn Ser
            500                 505                 510

Phe Lys Ala Asp Val Lys Gly His Gly Ala Thr Asn Asp Leu Thr
            515                 520                 525

Phe Thr Glu Glu Val Asp Met Lys Glu Met Glu Lys Ala Leu Gln
            530                 535                 540

Glu Arg Asp Tyr Ile Phe Gly Asn Tyr Ile Glu Arg Leu Trp Ala
            545                 550                 555

Tyr Leu Thr Ile Glu Gln Leu Leu Glu Lys Arg Lys Asn Ala His
            560                 565                 570

Gly Glu Glu Lys Glu Asn Leu Thr Ala Arg Ala Leu Asp Leu Ser
            575                 580                 585

Leu Lys Tyr His Phe Val Thr Pro Leu Thr Ser Met Val Val Thr
            590                 595                 600

Lys Pro Glu Asp Asn Glu Asp Glu Arg Ala Ile Ala Asp Lys Pro
            605                 610                 615

Gly Glu Asp Ala Glu Ala Thr Pro Val Ser Pro Ala Met Ser Tyr
            620                 625                 630

Leu Thr Ser Tyr Gln Pro Pro Gln Asn Pro Tyr Tyr Tyr Val Asp
            635                 640                 645

Gly Asp Pro His Phe Ile Ile Gln Ile Pro Glu Lys Asp Asp Ala
            650                 655                 660

Leu Cys Phe Asn Ile Asp Glu Ala Pro Gly Thr Val Leu Arg Leu
            665                 670                 675

Ile Gln Asp Ala Val Thr Gly Leu Thr Val Asn Gly Gln Ile Thr
            680                 685                 690

Gly Asp Lys Arg Gly Ser Pro Asp Ser Lys Thr Arg Lys Thr Tyr
            695                 700                 705

Phe Gly Lys Leu Gly Ile Arg Asn Ala Gln Met Asp Phe Gln Val
            710                 715                 720

Glu Val Thr Thr Glu Lys Ile Thr Cys Gly Thr Gly Arg Ala Ser
            725                 730                 735
```

-continued

```
Thr Phe Ser Trp Leu Asp Thr Val Thr Val Thr Gln Asp Gly Leu
                740             745             750
Ser Met Met Ile Asn Arg Lys Asn Met Val Val Ser Phe Gly Asp
                755             760             765
Gly Val Thr Phe Val Val Leu His Gln Val Trp Lys Lys His
                770             775             780
Pro Val His Arg Asp Phe Leu Gly Phe Tyr Val Val Asp Ser His
                785             790             795
Arg Met Ser Ala Gln Thr His Gly Leu Leu Gly Gln Phe Phe Gln
                800             805             810
Pro Phe Asp Phe Lys Val Ser Asp Ile Arg Pro Gly Ser Asp Pro
                815             820             825
Thr Lys Pro Asp Ala Thr Leu Val Val Lys Asn His Gln Leu Ile
                830             835             840
Val Thr Arg Gly Ser Gln Lys Asp Tyr Arg Lys Asp Ala Ser Ile
                845             850             855
Gly Thr Lys Val Val Cys Trp Phe Val His Asn Asn Gly Glu Gly
                860             865             870
Leu Ile Asp Gly Val His Thr Asp Tyr Ile Val Pro Asn Leu Phe
                875             880             885
```

GROWTH-ASSOCIATED PROTEASE INHIBITOR HEAVY CHAIN PRECURSOR

This application is a divisional application of U.S. application Ser. No. 09/074,579, filed May 7, 1998, now U.S. Pat. No. 6,001,596.

FIELD OF THE INVENTION

This invention relates to nucleic acid and amino acid sequences of a growth-associated protease inhibitor heavy chain precursor and to the use of these sequences in the diagnosis, treatment, and prevention of reproductive, developmental, neoplastic, and immunological disorders.

BACKGROUND OF THE INVENTION

Proteolytic processing is an essential component of normal cell growth, differentiation, remodeling, and homeostasis. The cleavage of peptide bonds within cells is necessary for the maturation of precursor proteins to their active form, the removal of signal sequences from targeted proteins, the degradation of incorrectly folded proteins, and the controlled turnover of peptides within the cell. Proteases participate in apoptosis, antigen presentation, inflammation, tissue remodeling during embryonic development, wound healing, and normal growth. They are necessary components of bacterial, parasitic, and viral invasion and replication within a host. Four principal categories of mammalian proteases have been identified based on active site structure, mechanism of action, and overall three-dimensional structure. (Beynon, R. J. and Bond, J. S. (1994) *Proteolytic Enzymes: A Practical Approach*, Oxford University Press, New York, N.Y., pp. 1–5.)

The serine proteases (SPs) are a large family of proteolytic enzymes that include the digestive enzymes, trypsin and chymotrypsin; components of the complement cascade and of the blood-clotting cascade; and enzymes that control the degradation and turnover of macromolecules of the extracellular matrix. SPs are so named because of the presence of a serine residue found in the active catalytic site for protein cleavage. The active site of all SP is composed of a triad of residues including the aforementioned serine, an aspartate, and a histidine residue. SPs have a wide range of substrate specificities and can be subdivided into subfamilies on the basis of these specificities. The main sub-families are trypases which cleave after arginine or lysine; aspases which cleave after aspartate; chymases which cleave after phenylalanine or leucine; metases which cleavage after methionine; and serases which cleave after serine.

The plasma inter-α-trypsin inhibitor family molecules are serine protease inhibitors (serpins) composed of a 240 kDa plasma protein complex of at least five different types of glycoproteins. These glycoproteins consist of four heavy (H) chains and one 30 kDa light (L) chain named H1, H2, H3, H4, and L, and are independently synthesized and proteolytically processed from precursor proteins. (Daveau, M. et al. (1998) Arch. Biochem. Biophys. 350:315–323; and Salier, J. P. et al. (1992) Mamm. Genome 2:233–239.) The plasma inter-α-trypsin inhibitor light chains have sequence similarity to the Kunitz trypsin inhibitors which appear to be present in all vertebrates. (Salier, J. P. (1990) Trends Biochem. Sci. 15:435–439.) Some examples of the Kunitz trypsin inhibitors are tissue factor pathway inhibitor, which regulates tissue factor-induced coagulation, and protease nexin-2, which regulates serum coagulation factor XIa. (Broze, G. J. (1995) Annu. Rev. Med. 46:103–112; and Wagner, S. L et al. (1993) Brain Res. 626:90–98.) The heavy chain precursors encode a signal peptide sequence and the mature chain. Other plasma inter-α-trypsin inhibitor heavy chains have been described in human and rodents. (Bourguignon, J. et al. (1993) Eur. J. Biochem.212:771–776; Salier, 1992, supra; and Salier, J. P. (1996) Biochem. J. 315:1–9.) Proteases and protease inhibitory molecules may contain amino acid sequence motifs which determine protein-protein interactions, such as the potential metal-binding site of von Willebrand factor type A3 (vWFA3) motif, glycine-amino acid-serine-amino acid-serine. This motif is also required for ligand interaction in the homologous I-type domains of integrins CR3 and LFA-1. (Huizinga, E. G. (1997) Structure 5:1147–1156.)

The expression of the rat plasma inter-α-trypsin inhibitor genes is regulated by inflammation in vivo. The genes are predominantly expressed in the rat liver, but H2 and H3 mRNA is also present in brain, intestine, and stomach. (Daveau, supra.)

Protease inhibitors play a major role in the regulation of the activity and effect of proteases. They have been shown to control pathogenesis in animal models of proteolytic disorders and in the treatment of HIV. (Murphy, G. (1991) Agents Actions Suppl. 35:69–76; and Pakyz, A. and Isreal, D. (1997) J. Am. Pharm. Assoc. (Wash.) NS37:543– 551.)

The discovery of a new growth-associated protease inhibitor heavy chain precursor and the polynucleotides encoding it satisfies a need in the art by providing new compositions which are useful in the diagnosis, treatment, and prevention of reproductive, developmental, neoplastic, and immunological disorders.

SUMMARY OF THE INVENTION

The invention is based on the discovery of a new human growth-associated protease inhibitor heavy chain precursor (GAPIP), the polynucleotides encoding GAPIP, and the use of these compositions for the diagnosis, treatment, or prevention of reproductive, developmental, neoplastic, and immunological disorders.

The invention features a substantially purified polypeptide comprising the amino acid sequence of SEQ ID NO: 1 or a fragment of SEQ ID NO: 1.

The invention further provides a substantially purified variant having at least 90% amino acid sequence identity to the amino acid sequence of SEQ ID NO: 1 or a fragment of SEQ ID NO: 1. The invention also provides an isolated and purified polynucleotide encoding the polypeptide comprising the sequence of SEQ ID NO: 1 or a fragment of SEQ ID NO: 1. The invention also includes an isolated and purified polynucleotide variant having at least 90% polynucleotide sequence identity to the polynucleotide encoding the polypeptide comprising the amino acid sequence of SEQ ID NO: 1 or a fragment of SEQ ID NO: 1.

The invention further provides an isolated and purified polynucleotide which hybridizes under stringent conditions to the polynucleotide encoding the polypeptide comprising the amino acid sequence of SEQ ID NO: 1 or a fragment of SEQ ID NO: 1, as well as an isolated and purified polynucleotide which is complementary to the polynucleotide encoding the polypeptide comprising the amino acid sequence of SEQ ID NO: 1 or a fragment of SEQ ID NO: 1.

The invention also provides an isolated and purified polynucleotide comprising the polynucleotide sequence of SEQ ID NO:2 or a fragment of SEQ ID NO:2, and an isolated and purified polynucleotide variant having at least 90% polynucleotide sequence identity to the polynucleotide comprising the polynucleotide sequence of SEQ ID NO:2 or a fragment of SEQ ID NO:2. The invention also provides an isolated and purified polynucleotide having a sequence complementary to the polynucleotide comprising the polynucleotide sequence of SEQ ID NO:2 or a fragment of SEQ ID NO:2.

The invention further provides an expression vector comprising at least a fragment of the polynucleotide encoding the polypeptide comprising the sequence of SEQ ID NO: 1 or a fragment of SEQ ID NO: 1. In another aspect, the expression vector is contained within a host cell.

The invention also provides a method for producing a polypeptide comprising the amino acid sequence of SEQ ID NO: 1 or a fragment of SEQ ID NO: 1, the method comprising the steps of: (a) culturing the host cell comprising an expression vector containing at least a fragment of a polynucleotide encoding the polypeptide comprising the amino acid sequence of SEQ ID NO: 1 or a fragment of SEQ ID NO: 1 under conditions suitable for the expression of the polypeptide; and (b) recovering the polypeptide from the host cell culture.

The invention also provides a pharmaceutical composition comprising a substantially purified polypeptide having the sequence of SEQ ID NO: 1 or a fragment of SEQ ID NO: 1 in conjunction with a suitable pharmaceutical carrier.

The invention further includes a purified antibody which binds to a polypeptide comprising the sequence of SEQ ID NO: 1 or a fragment of SEQ ID NO: 1, as well as a purified agonist and a purified antagonist of the polypeptide.

The invention also provides a method for treating or preventing a reproductive disorder, the method comprising administering to a subject in need of such treatment an effective amount of a pharmaceutical composition comprising substantially purified polypeptide having the amino acid sequence of SEQ ID NO: 1 or a fragment of SEQ ID NO: 1.

The invention also provides a method for treating or preventing a developmental disorder, the method comprising administering to a subject in need of such treatment an effective amount of a pharmaceutical composition comprising substantially purified polypeptide having the amino acid sequence of SEQ ID NO: 1 or a fragment of SEQ ID NO: 1.

The invention also provides a method for treating or preventing a neoplastic disorder, the method comprising administering to a subject in need of such treatment an effective amount of an antagonist of the polypeptide having the amino acid sequence of SEQ ID NO: 1 or a fragment of SEQ ID NO: 1.

The invention also provides a method for treating or preventing an immunological disorder, the method comprising administering to a subject in need of such treatment an effective amount of an antagonist of the polypeptide having the amino acid sequence of SEQ ID NO: 1 or a fragment of SEQ ID NO: 1.

The invention also provides a method for detecting a polynucleotide encoding a polypeptide comprising the amino acid sequence of SEQ ID NO: 1 or a fragment of SEQ ID NO: 1 in a biological sample containing nucleic acids, the method comprising the steps of: (a) hybridizing the complement of the polynucleotide encoding the polypeptide comprising the amino acid sequence of SEQ ID NO:1 or a fragment of SEQ ID NO:1 to at least one of the nucleic acids of the biological sample, thereby forming a hybridization complex; and (b) detecting the hybridization complex, wherein the presence of the hybridization complex correlates with the presence of a polynucleotide encoding the polypeptide comprising the amino acid sequence of SEQ ID NO: 1 or a fragment of SEQ ID NO: 1 in the biological sample. In one aspect, the nucleic acids of the biological sample are amplified by the polymerase chain reaction prior to the hybridizing step.

BRIEF DESCRIPTION OF THE FIGURES

FIGS. 1A, 1B, 1C, 1D, 1E, 1F, 1G, 1H, 1I, and 1J show the amino acid sequence (SEQ ID NO: 1) and nucleic acid sequence (SEQ ID NO:2) of GAPIP. The alignment was produced using MacDNASIS PRO™ software (Hitachi Software Engineering Co. Ltd., San Bruno, Calif.).

Figure 2C:
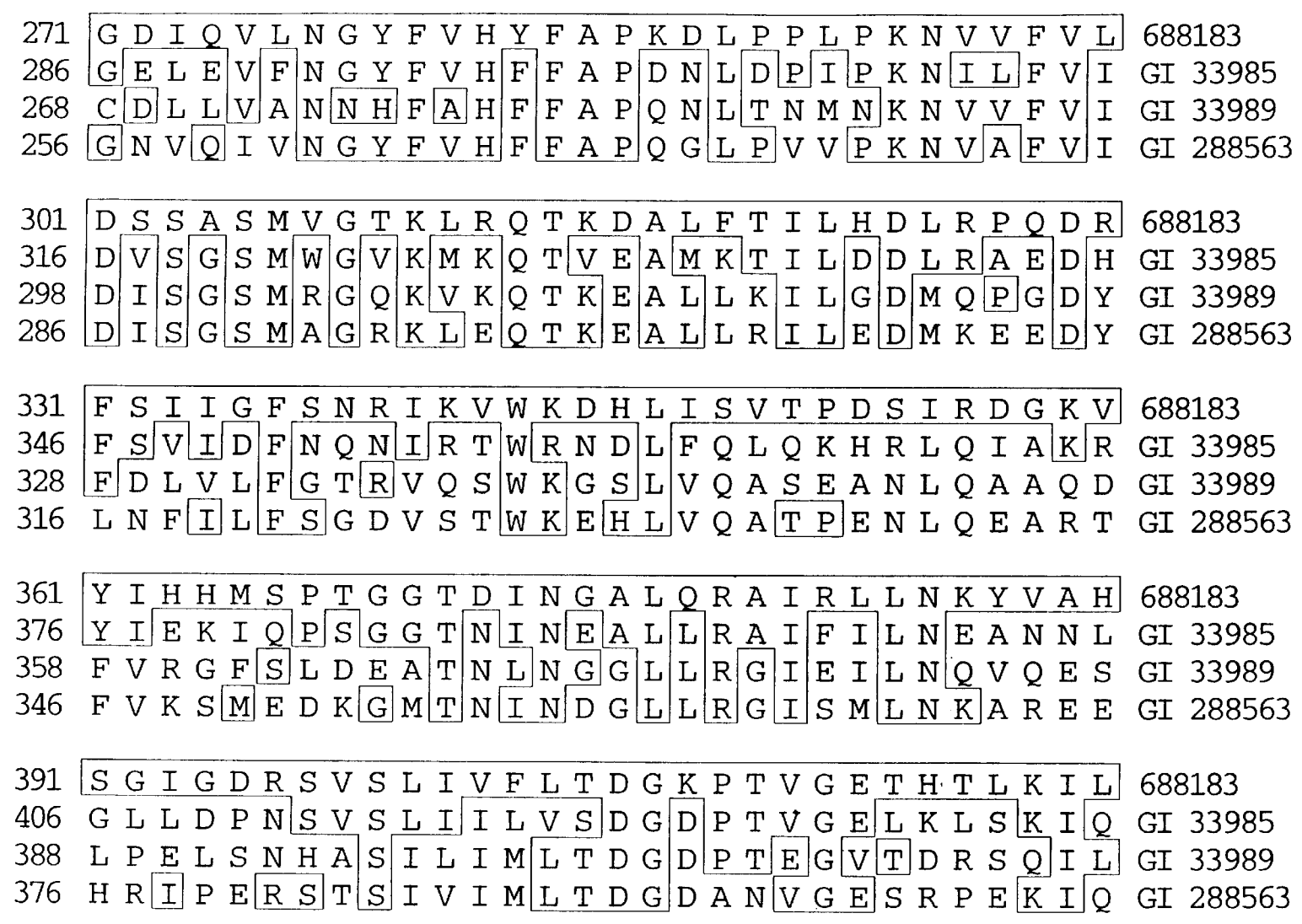

FIGS. 2A, 2B, 2C, 2D, 2E, 2F, and 2G show the amino acid sequence alignments among GAPIP (688183; SEQ ID NO:1), human pre-inter-α-trypsin inhibitor (GI 33985; SEQ ID NO:3), human pre-inter-α-trypsin inhibitor heavy chain H1 (GI 33989; SEQ ID NO:4), and human pre-inter-α-trypsin inhibitor heavy chain H3 (GI 288563; SEQ ID NO:5), produced using the multisequence alignment program of LASERGENET™ software (DNASTAR Inc, Madison Wis.).

DESCRIPTION OF THE INVENTION

Figure 3:
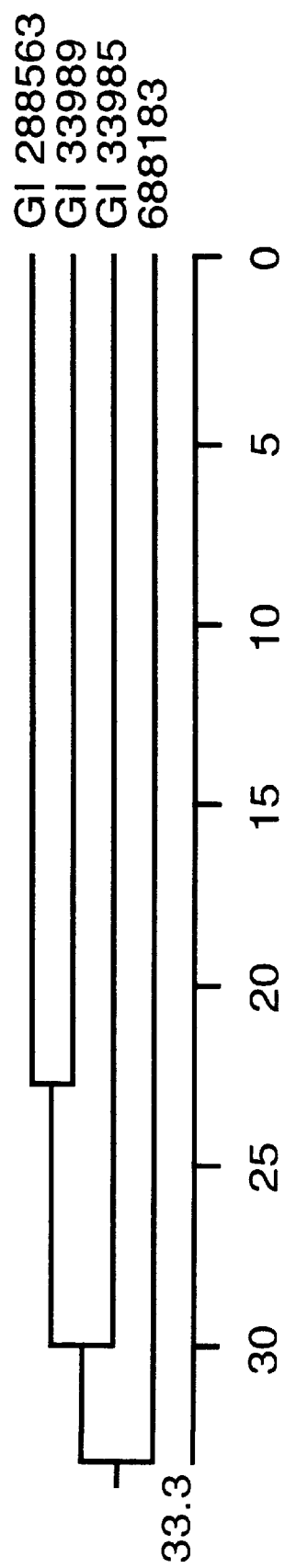
FIG. 3 shows the amino acid sequence phylogenic tree among GAPIP (688183; SEQ ID NO:1), human pre-inter-α-trypsin inhibitor (GI 33985; SEQ ID NO:3), human pre-inter-α-trypsin inhibitor heavy chain H1 (GI 33989; SEQ ID NO:4), and human pre-inter-α-trypsin inhibitor heavy chain H3 (GI 288563; SEQ ID NO:5), produced using the multisequence alignment program of LASERGENE™ software (DNASTAR Inc, Madison Wis.).

Before the present proteins, nucleotide sequences, and methods are described, it is understood that this invention is not limited to the particular methodology, protocols, cell lines, vectors, and reagents described, as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a," "an," and "the" include plural reference unless the context clearly dictates otherwise. Thus, for example, a reference to "a host cell" includes a plurality of such host cells, and a reference to "an antibody" is a reference to one or more antibodies and equivalents thereof known to those skilled in the art, and so forth.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications mentioned herein are cited for the purpose of describing and disclosing the cell lines, vectors, and methodologies which are reported in the publications and which might be used in connection with the invention. Nothing herein is to be construed as an admission that the invention is not entitled to antedate such disclosure by virtue of prior invention.

Definitions

"GAPIP," as used herein, refers to the amino acid sequences of substantially purified GAPIP obtained from any species, particularly a mammalian species, including bovine, ovine, porcine, murine, equine, and preferably the human species, from any source, whether natural, synthetic, semi-synthetic, or recombinant.

The term "agonist," as used herein, refers to a molecule which, when bound to GAPIP, increases or prolongs the duration of the effect of GAPIP. Agonists may include proteins, nucleic acids, carbohydrates, or any other molecules which bind to and modulate the effect of GAPIP.

An "allelic variant," as this term is used herein, is an alternative form of the gene encoding GAPIP. Allelic variants may result from at least one mutation in the nucleic acid sequence and may result in altered mRNAs or in polypeptides whose structure or function may or may not be altered. Any given natural or recombinant gene may have none, one, or many allelic forms. Common mutational changes which give rise to allelic variants are generally ascribed to natural deletions, additions, or substitutions of nucleotides. Each of these types of changes may occur alone, or in combination with the others, one or more times in a given sequence.

"Altered" nucleic acid sequences encoding GAPIP, as described herein, include those sequences with deletions, insertions, or substitutions of different nucleotides, resulting in a polynucleotide the same as GAPIP or a polypeptide with at least one functional characteristic of GAPIP. Included within this definition are polymorphisms which may or may not be readily detectable using a particular oligonucleotide probe of the polynucleotide encoding GAPIP, and improper or unexpected hybridization to allelic variants, with a locus other than the normal chromosomal locus for the polynucleotide sequence encoding GAPIP. The encoded protein may also be "altered," and may contain deletions, insertions, or substitutions of amino acid residues which produce a silent change and result in a functionally equivalent GAPIP. Deliberate amino acid substitutions may be made on the basis of similarity in polarity, charge, solubility, hydrophobicity, hydrophilicity, and/or the amphipathic nature of the residues, as long as the biological or immunological activity of GAPIP is retained. For example, negatively charged amino acids may include aspartic acid and glutamic acid, positively charged amino acids may include lysine and arginine, and amino acids with uncharged polar head groups having similar hydrophilicity values may include leucine, isoleucine, and valine; glycine and alanine; asparagine and glutamine; serine and threonine; and phenylalanine and tyrosine.

The terms "amino acid" or "amino acid sequence," as used herein, refer to an oligopeptide, peptide, polypeptide, or protein sequence, or a fragment of any of these, and to naturally occurring or synthetic molecules. In this context, "fragments," "immunogenic fragments," or "antigenic fragments" refer to fragments of GAPIP which are preferably about 5 to about 15 amino acids in length, most preferably 14 amino acids, and which retain some biological activity or immunological activity of GAPIP. Where "amino acid sequence" is recited herein to refer to an amino acid sequence of a naturally occurring protein molecule, "amino acid sequence" and like terms are not meant to limit the amino acid sequence to the complete native amino acid sequence associated with the recited protein molecule.

"Amplification," as used herein, relates to the production of additional copies of a nucleic acid sequence. Amplification is generally carried out using polymerase chain reaction (PCR) technologies well known in the art. (See, e.g., Dieffenbach, C. W. and G. S. Dveksler (1995) *PCR Primer, a Laboratory Manual*, Cold Spring Harbor Press, Plainview, N.Y., pp. 1–5.)

The term "antagonist," as it is used herein, refers to a molecule which, when bound to GAPIP, decreases the amount or the duration of the effect of the biological or immunological activity of GAPIP. Antagonists may include proteins, nucleic acids, carbohydrates, antibodies, or any other molecules which decrease the effect of GAPIP.

As used herein, the term "antibody" refers to intact molecules as well as to fragments thereof, such as Fab, $F(ab')_2$, and Fv fragments, which are capable of binding the epitopic determinant. Antibodies that bind GAPIP polypeptides can be prepared using intact polypeptides or using fragments containing small peptides of interest as the immunizing antigen. The polypeptide or oligopeptide used to immunize an animal (e.g., a mouse, a rat, or a rabbit) can be derived from the translation of RNA, or synthesized chemically, and can be conjugated to a carrier protein if desired. Commonly used carriers that are chemically coupled to peptides include bovine serum albumin, thyroglobulin, and keyhole limpet hemocyanin (KLH). The coupled peptide is then used to immunize the animal.

The term "antigenic determinant," as used herein, refers to that fragment of a molecule (i.e., an epitope) that makes contact with a particular antibody. When a protein or a fragment of a protein is used to immunize a host animal, numerous regions of the protein may induce the production of antibodies which bind specifically to antigenic determinants (given regions or three-dimensional structures on the protein). An antigenic determinant may compete with the intact antigen (i.e., the immunogen used to elicit the immune response) for binding to an antibody.

The term "antisense," as used herein, refers to any composition containing a nucleic acid sequence which is complementary to the "sense" strand of a specific nucleic acid sequence. Antisense molecules may be produced by any method including synthesis or transcription. Once introduced into a cell, the complementary nucleotides combine with natural sequences produced by the cell to form duplexes and to block either transcription or translation. The designation "negative" can refer to the antisense strand, and the designation "positive" can refer to the sense strand.

As used herein, the term "biologically active," refers to a protein having structural, regulatory, or biochemical functions of a naturally occurring molecule. Likewise, "immunologically active" refers to the capability of the natural, recombinant, or synthetic GAPIP, or of any oligopeptide thereof, to induce a specific immune response in appropriate animals or cells and to bind with specific antibodies.

The terms "complementary" or "complementarity," as used herein, refer to the natural binding of polynucleotides under permissive salt and temperature conditions by base pairing. For example, the sequence "A-G-T" binds to the complementary sequence "T-C-A." Complementarity between two single-stranded molecules may be "partial," such that only some of the nucleic acids bind, or it may be "complete," such that total complementarity exists between the single stranded molecules. The degree of complementarity between nucleic acid strands has significant effects on the efficiency and strength of the hybridization between the nucleic acid strands. This is of particular importance in amplification reactions, which depend upon binding between nucleic acids strands, and in the design and use of peptide nucleic acid (PNA) molecules.

A "composition comprising a given polynucleotide sequence" or a "composition comprising a given amino acid sequence," as these terms are used herein, refer broadly to any composition containing the given polynucleotide or amino acid sequence. The composition may comprise a dry formulation, an aqueous solution, or a sterile composition. Compositions comprising polynucleotide sequences encoding GAPIP or fragments of GAPIP may be employed as hybridization probes. The probes may be stored in freeze-dried form and may be associated with a stabilizing agent such as a carbohydrate. In hybridizations, the probe may be deployed in an aqueous solution containing salts, e.g., NaCl, detergents, e.g., sodium dodecyl sulfate (SDS), and other components, e.g., Denhardt's solution, dry milk, salmon sperm DNA, etc.

"Consensus sequence," as used herein, refers to a nucleic acid sequence which has been resequenced to resolve uncalled bases, extended using XL-PCR™ (Perkin Elmer, Norwalk, Conn.) in the 5' and/or the 3' direction, and resequenced, or which has been assembled from the overlapping sequences of more than one Incyte Clone using a computer program for fragment assembly, such as the GEL-VIEW™ Fragment Assembly system (GCG, Madison, Wis.). Some sequences have been both extended and assembled to produce the consensus sequence.

As used herein, the term "correlates with expression of a polynucleotide" indicates that the detection of the presence of nucleic acids, the same or related to a nucleic acid sequence encoding GAPIP, by Northern analysis is indicative of the presence of nucleic acids encoding GAPIP in a sample, and thereby correlates with expression of the transcript from the polynucleotide encoding GAPIP.

A "deletion," as the term is used herein, refers to a change in the amino acid or nucleotide sequence that results in the absence of one or more amino acid residues or nucleotides.

The term "derivative," as used herein, refers to the chemical modification of a polypeptide sequence, or a polynucleotide sequence. Chemical modifications of a polynucleotide sequence can include, for example, replacement of hydrogen by an alky, acyl, or amino group. A derivative polynucleotide encodes a polypeptide which retains at least one biological or immunological function of the natural molecule. A derivative polypeptide is one modified by glycosylation, pegylation, or any similar process that retains at least one biological or immunological function of the polypeptide from which it was derived.

The term "similarity," as used herein, refers to a degree of complementarity. There may be partial similarity or complete similarity. The word "identity" may substitute for the word "similarity." A partially complementary sequence that at least partially inhibits an identical sequence from hybridizing to a target nucleic acid is referred to as "substantially similar." The inhibition of hybridization of the completely complementary sequence to the target sequence may be examined using a hybridization assay (Southern or Northern blot, solution hybridization, and the like) under conditions of reduced stringency. A substantially similar sequence or hybridization probe will compete for and inhibit the binding of a completely similar (identical) sequence to the target sequence under conditions of reduced stringency. This is not to say that conditions of reduced stringency are such that non-specific binding is permitted, as reduced stringency conditions require that the binding of two sequences to one another be a specific (i.e., a selective) interaction. The absence of non-specific binding may be tested by the use of a second target sequence which lacks even a partial degree of complementarity (e.g., less than about 30% similarity or identity). In the absence of non-specific binding, the substantially similar sequence or probe will not hybridize to the second non-complementary target sequence.

The phrases "percent identity" or "% identity" refer to the percentage of sequence similarity found in a comparison of two or more amino acid or nucleic acid sequences. Percent identity can be determined electronically, e.g., by using the MegAlign™ program (DNASTAR, Inc., Madison Wis.). The MegAlign™ program can create alignments between two or more sequences according to different methods, e.g., the clustal method. (See, e.g., Higgins, D. G. and P. M. Sharp (1988) Gene 73:237–244.) The clustal algorithm groups sequences into clusters by examining the distances between all pairs. The clusters are aligned pairwise and then in groups. The percentage similarity between two amino acid sequences, e.g., sequence A and sequence B, is calculated by dividing the length of sequence A, minus the number of gap residues in sequence A, minus the number of gap residues in sequence B, into the sum of the residue matches between sequence A and sequence B, times one hundred. Gaps of low or of no similarity between the two amino acid sequences are not included in determining percentage similarity. Percent identity between nucleic acid sequences can also be counted or calculated by other methods known in the art, e.g., the Jotun Hein method. (See, e.g., Hein, J. (1990) Methods Enzymol. 183:626–645.) Identity between sequences can also be determined by other methods known in the art, e.g., by varying hybridization conditions.

"Human artificial chromosomes" (HACs), as described herein, are linear microchromosomes which may contain DNA sequences of about 6 kb to 10 Mb in size, and which contain all of the elements required for stable mitotic chromosome segregation and maintenance. (See, e.g., Harrington, J. J. et al. (1997) Nat Genet. 15:345–355.)

The term "humanized antibody," as used herein, refers to antibody molecules in which the amino acid sequence in the non-antigen binding regions has been altered so that the antibody more closely resembles a human antibody, and still retains its original binding ability.

"Hybridization," as the term is used herein, refers to any process by which a strand of nucleic acid binds with a complementary strand through base pairing.

As used herein, the term "hybridization complex" refers to a complex formed between two nucleic acid sequences by virtue of the formation of hydrogen bonds between complementary bases. A hybridization complex may be formed in solution (e.g., $C_0t$ or $R_0t$ analysis) or formed between one nucleic acid sequence present in solution and another nucleic acid sequence immobilized on a solid support (e.g., paper, membranes, filters, chips, pins or glass slides, or any other appropriate substrate to which cells or their nucleic acids have been fixed).

The words "insertion" or "addition," as used herein, refer to changes in an amino acid or nucleotide sequence resulting in the addition of one or more amino acid residues or nucleotides, respectively, to the sequence found in the naturally occurring molecule.

"Immune response" can refer to conditions associated with inflammation, trauma, immune disorders, or infectious or genetic disease, etc. These conditions can be characterized by expression of various factors, e.g., cytokines, chemokines, and other signaling molecules, which may affect cellular and systemic defense systems.

The term "microarray," as used herein, refers to an arrangement of distinct polynucleotides arrayed on a substrate, e.g., paper, nylon or any other type of membrane, filter, chip, glass slide, or any other suitable solid support.

The terms "element" or "array element" as used herein in a microarray context, refer to hybridizable polynucleotides arranged on the surface of a substrate.

The term "modulate," as it appears herein, refers to a change in the activity of GAPIP.

For example, modulation may cause an increase or a decrease in protein activity, binding characteristics, or any other biological, functional, or immunological properties of GAPIP.

The phrases "nucleic acid" or "nucleic acid sequence," as used herein, refer to a nucleotide, oligonucleotide, polynucleotide, or any fragment thereof. These phrases also refer to DNA or RNA of genomic or synthetic origin which may be single-stranded or double-stranded and may represent the sense or the antisense strand, to peptide nucleic acid (PNA), or to any DNA-like or RNA-like material. In this context, "fragments" refers to those nucleic acid sequences which, when translated, would produce polypeptides retaining some functional characteristic, e.g., antigenicity, or structural domain characteristic, e.g., ATP-binding site, of the full-length polypeptide.

The terms "operably associated" or "operably linked," as used herein, refer to functionally related nucleic acid sequences. A promoter is operably associated or operably linked with a coding sequence if the promoter controls the translation of the encoded polypeptide. While operably associated or operably linked nucleic acid sequences can be contiguous and in the same reading frame, certain genetic elements, e.g., repressor genes, are not contiguously linked to the sequence encoding the polypeptide but still bind to operator sequences that control expression of the polypeptide.

The term "oligonucleotide," as used herein, refers to a nucleic acid sequence of at least about 6 nucleotides to 60 nucleotides, preferably about 15 to 30 nucleotides, and most preferably about 20 to 25 nucleotides, which can be used in PCR amplification or in a hybridization assay or microarray. As used herein, the term "oligonucleotide" is substantially equivalent to the terms "amplimer," "primer," "oligomer," and "probe," as these terms are commonly defined in the art.

"Peptide nucleic acid" (PNA), as used herein, refers to an antisense molecule or anti-gene agent which comprises an oligonucleotide of at least about 5 nucleotides in length linked to a peptide backbone of amino acid residues ending in lysine. The terminal lysine confers solubility to the composition. PNAs preferentially bind complementary single stranded DNA or RNA and stop transcript elongation, and may be pegylated to extend their lifespan in the cell. (See, e.g., Nielsen, P. E. et al. (1993) Anticancer Drug Des. 8:53–63.)

The term "sample," as used herein, is used in its broadest sense. A biological sample suspected of containing nucleic acids encoding GAPIP, or fragments thereof, or GAPIP itself, may comprise a bodily fluid; an extract from a cell, chromosome, organelle, or membrane isolated from a cell; a cell; genomic DNA, RNA, or cDNA, in solution or bound to a solid support; a tissue; a tissue print; etc.

As used herein, the terms "specific binding" or "specifically binding" refer to that interaction between a protein or peptide and an agonist, an antibody, or an antagonist. The interaction is dependent upon the presence of a particular structure of the protein, e.g., the antigenic determinant or epitope, recognized by the binding molecule. For example, if an antibody is specific for epitope "A," the presence of a polypeptide containing the epitope A, or the presence of free unlabeled A, in a reaction containing free labeled A and the antibody will reduce the amount of labeled A that binds to the antibody.

As used herein, the term "stringent conditions" refers to conditions which permit hybridization between polynucleotides and the claimed polynucleotides. Stringent conditions can be defined by salt concentration, the concentration of organic solvent (e.g., formamide), temperature, and other conditions well known in the art. In particular, stringency can be increased by reducing the concentration of salt, increasing the concentration of formamide, or raising the hybridization temperature.

For example, stringent salt concentration will ordinarily be less than about 750 mM NaCl and 75 mM trisodium citrate, preferably less than about 500 mM NaCl and 50 mM trisodium citrate, and most preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and most preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 μg/ml denatured salmon sperm DNA (ssDNA). In a most preferred embodiment, hybridization will occur at 42° C. in 250 mM NaCl, 25 mM trisodium citrate, 1% SDS, 50% formamide, and 200 μg/ml ssDNA. Useful variations on these conditions will be readily apparent to those skilled in the art.

The washing steps which follow hybridization can also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include temperature of at least about 25° C., more preferably of at least about 42° C., and most preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42° C. in 15 mM NaCl, 1.5 mM trisodium citrate, and 0.1% SDS. In a most preferred embodiment, wash steps will occur at 68° C. in 15 mM NaCl, 1.5 mM trisodium citrate, and 0.1% SDS. Additional variations on these conditions will be readily apparent to those skilled in the art.

The term "substantially purified," as used herein, refers to nucleic acid or amino acid sequences that are removed from their natural environment and are isolated or separated, and are at least about 60% free, preferably about 75% free, and most preferably about 90% free from other components with which they are naturally associated.

A "substitution," as used herein, refers to the replacement of one or more amino acids or nucleotides by different amino acids or nucleotides, respectively.

"Transformation," as defined herein, describes a process by which exogenous DNA enters and changes a recipient cell. Transformation may occur under natural or artificial conditions according to various methods well known in the art, and may rely on any known method for the insertion of foreign nucleic acid sequences into a prokaryotic or eukaryotic host cell. The method for transformation is selected based on the type of host cell being transformed and may include, but is not limited to, viral infection, electroporation, heat shock, lipofection, and particle bombardment. The term "transformed" cells includes stably transformed cells in which the inserted DNA is capable of replication either as an autonomously replicating plasmid or as part of the host chromosome, as well as transiently transformed cells which express the inserted DNA or RNA for limited periods of time.

A "variant" of GAPIP, as used herein, refers to an amino acid sequence that is altered by one or more amino acids. The variant may have "conservative" changes, wherein a substituted amino acid has similar structural or chemical properties (e.g., replacement of leucine with isoleucine). More rarely, a variant may have "nonconservative" changes (e.g., replacement of glycine with tryptophan). Analogous minor variations may also include amino acid deletions or insertions, or both. Guidance in determining which amino acid residues may be substituted, inserted, or deleted without abolishing biological or immunological activity may be found using computer programs well known in the art, for example, LASERGENE™ software.

The Invention

The invention is based on the discovery of a new human growth-associated protease inhibitor heavy chain precursor (GAPIP), the polynucleotides encoding GAPIP, and the use of these compositions for the diagnosis, treatment, or prevention of reproductive, developmental, neoplastic, and immunological disorders.

Nucleic acids encoding the GAPIP of the present invention were first identified in Incyte Clone 688183 from the uterus cDNA library (UTRSNOT02) using a computer search, e.g., BLAST, for amino acid sequence alignments. A consensus sequence, SEQ ID NO:2, was derived from the following overlapping and/or extended nucleic acid sequences: Incyte Clones 688183 (UTRSNOT02), 3043969 (HEAANOT01), 3112673 (BRSTNOT17), 3052595 (LNODNOT08), 789100 (PROSTUT03), 785182 (PROSNOT05), 1505061 and 1505717 (BRAITUT07), 1794195 and 1795083 (PROSTUT05), 2125590 (BRSTNOT07), 1558218 (SPLNNOT04), 1361072 (LUNGNOT12), and 1964439 (BRSTNOT04).

In one embodiment, the invention encompasses a polypeptide comprising the amino acid sequence of SEQ ID NO: 1, as shown in FIGS. 1A, 1B, 1C, 1D, 1E, 1F, IG, 1H, 1I, and 1J. GAPIP is 942 amino acids in length and has eight potential N-glycosylation sites at residues N97, N 127, N231, N421, N508, N776, N795, and N862; twelve potential casein kinase II phosphorylation sites at residues S17, S28, T112, T129, S158, S269, S354, T410, T581, S592, T676, and S754; two potential glycosaminoglycan attachment sites at residues S213 and S391; seventeen potential protein kinase C phosphorylation sites at residues S55, S70, T112, S175, S182, S213, S337, S354, T416, T458, S535, S559, T581, S611, S620, S651, and T880; one potential tyrosine kinase phosphorylation site at residue Y919; a potential signal peptide sequence from M1 to C14; and a vWFA3 domain, which contains the potential metal-binding site glycine-amino acid-serine-amino acid-serine, from N295 to N440. As shown in FIGS. 2A, 2B, 2C, 2D, 2E, 2F, and 2G, GAPIP has chemical and structural similarity with human pre-inter-α-trypsin inhibitor (GI 33985; SEQ ID NO:3), human pre-inter-α-trypsin inhibitor heavy chain H1 (GI 33989; SEQ ID NO:4), and human pre-inter-α-trypsin inhibitor heavy chain H3 (GI 288563; SEQ ID NO:5). In particular, GAPIP and human pre-inter-α-trypsin inhibitor share 28% identity, one potential N-glycosylation site, four potential casein kinase II phosphorylation sites, four potential protein kinase C phosphorylation sites, the potential signal peptide sequence, and the vWFA3 potential metal-binding site glycine-amino acid-serine-amino acid-serine. In addition, GAPIP and human pre-inter-α-trypsin inhibitor heavy chains H1 and H3 share 27% and 23% identity, respectively, one potential N-glycosylation site, four potential casein kinase II phosphorylation sites, five potential protein kinase C phosphorylation sites, the potential signal peptide sequence, and the vWFA3 potential metal-binding site glycine-amino acid-serine-amino acid-serine. As illustrated by FIG. 3, GAPIP and human pre-inter-α-trypsin inhibitor heavy chains share a common phylogenic heritage. A fragment of SEQ ID NO:2 from about nucleotide 982 to about nucleotide 1011 is useful, for example, for designing oligonucleotides or as a hybridization probe. Northern analysis shows the expression of this sequence in various libraries, at least 63% of which are immortalized or cancerous and at least 26% of which involve immune response. Of particular note is the expression of GAPIP in reproductive, gastrointestinal, nervous, and fetal tissues.

The invention also encompasses GAPIP variants. A preferred GAPIP variant is one which has at least about 80%, more preferably at least about 90%, and most preferably at least about 95% amino acid sequence identity to the GAPIP amino acid sequence, and which contains at least one functional or structural characteristic of GAPIP.

The invention also encompasses polynucleotides which encode GAPIP. In a particular embodiment, the invention encompasses a polynucleotide sequence comprising the sequence of SEQ ID NO:2, which encodes an GAPIP.

The invention also encompasses a variant of a polynucleotide sequence encoding GAPIP. In particular, such a variant polynucleotide sequence will have at least about 80%, more preferably at least about 90%, and most preferably at least about 95% polynucleotide sequence identity to the polynucleotide sequence encoding GAPIP. A particular aspect of the invention encompasses a variant of SEQ ID NO:2 which has at least about 80%, more preferably at least about 90%, and most preferably at least about 95% polynucleotide sequence identity to SEQ ID NO:2. Any one of the polynucleotide variants described above can encode an amino acid sequence which contains at least one functional or structural characteristic of GAPIP.

It will be appreciated by those skilled in the art that as a result of the degeneracy of the genetic code, a multitude of polynucleotide sequences encoding GAPIP, some bearing minimal similarity to the polynucleotide sequences of any known and naturally occurring gene, may be produced. Thus, the invention contemplates each and every possible variation of polynucleotide sequence that could be made by selecting combinations based on possible codon choices. These combinations are made in accordance with the standard triplet genetic code as applied to the polynucleotide sequence of naturally occurring GAPIP, and all such variations are to be considered as being specifically disclosed.

Although nucleotide sequences which encode GAPIP and its variants are preferably capable of hybridizing to the nucleotide sequence of the naturally occurring GAPIP under appropriately selected conditions of stringency, it may be advantageous to produce nucleotide sequences encoding GAPIP or its derivatives possessing a substantially different codon usage, e.g., inclusion of non-naturally occurring codons. Codons may be selected to increase the rate at which expression of the peptide occurs in a particular prokaryotic or eukaryotic host in accordance with the frequency with which particular codons are utilized by the host. Other reasons for substantially altering the nucleotide sequence encoding GAPIP and its derivatives without altering the encoded amino acid sequences include the production of RNA transcripts having more desirable properties, such as a greater half-life, than transcripts produced from the naturally occurring sequence.

The invention also encompasses production of DNA sequences which encode GAPIP and GAPIP derivatives, or fragments thereof, entirely by synthetic chemistry. After production, the synthetic sequence may be inserted into any of the many available expression vectors and cell systems using reagents well known in the art. Moreover, synthetic chemistry may be used to introduce mutations into a sequence encoding GAPIP or any fragment thereof.

Also encompassed by the invention are polynucleotide sequences that are capable of hybridizing to the claimed polynucleotide sequences, and, in particular, to those shown in SEQ ID NO:2, or a fragment of SEQ ID NO:2, under various conditions of stringency. (See, e.g., Wahl, G. M. and S. L. Berger (1987) Methods Enzymol. 152:399–407; Kimmel, A. R. (1987) Methods Enzymol. 152:507–511.)

Methods for DNA sequencing are well known and generally available in the art and may be used to practice any of the embodiments of the invention. The methods may employ such enzymes as the Klenow fragment of DNA polymerase I, Sequenase® (US Biochemical Corp., Cleveland, Ohio), Taq polymerase (Perkin Elmer), thermostable T7 polymerase (Amersham, Chicago, Ill.), or combinations of polymerases and proofreading exonucleases such as those found in the ELONGASE™ Amplification System (GIBCO BRL, Gaithersburg, Md.). Preferably, the process is automated with machines such as the Hamilton Micro Lab 2200 (Hamilton, Reno, Nev.), Peltier Thermal Cycler (PTC200; MJ Research, Watertown, Mass.) and the ABI Catalyst and 373 and 377 DNA Sequencers (Perkin Elmer).

The nucleic acid sequences encoding GAPIP may be extended utilizing a partial nucleotide sequence and employing various PCR-based methods known in the art to detect upstream sequences, such as promoters and regulatory elements. For example, one method which may be employed, restriction-site PCR, uses universal and nested primers to amplify unknown sequence from genomic DNA within a cloning vector. (See, e.g., Sarkar, G. (1993) PCR Methods Applic. 2:318–322.) Another method, inverse PCR, uses primers that extend in divergent directions to amplify unknown sequence from a circularized template. The template is derived from restriction fragments comprising a known genomic locus and surrounding sequences. (See, e.g., Triglia, T. et al. (1988) Nucleic Acids Res. 16:8186.) A third method, capture PCR, involves PCR amplification of DNA fragments adjacent to known sequences in human and yeast artificial chromosome DNA. (See, e.g., Lagerstrom, M. et al. (1991) PCR Methods Applic. 1:111–119.) In this method, multiple restriction enzyme digestions and ligations may be used to insert an engineered double-stranded sequence into a region of unknown sequence before performing PCR. Other methods which may be used to retrieve unknown sequences are known in the art. (See, e.g., Parker, J. D. et al. (1991) Nucleic Acids Res. 19:3055–306). Additionally, one may use PCR, nested primers, and PromoterFinder™ libraries to walk genomic DNA (Clontech, Palo Alto, Calif.). This procedure avoids the need to screen libraries and is useful in finding intron/exon junctions. For all PCR-based methods, primers may be designed using commercially available software, such as OLIGO™ 4.06 Primer Analysis software (National Biosciences Inc., Plymouth, Minn.) or another appropriate program, to be about 22 to 30 nucleotides in length, to have a GC content of about 50% or more, and to anneal to the template at temperatures of about 68° C. to 72° C.

When screening for full-length cDNAs, it is preferable to use libraries that have been size-selected to include larger cDNAs. In addition, random-primed libraries, which often include sequences containing the 5' regions of genes, are preferable for situations in which an oligo d(T) library does not yield a full-length cDNA. Genomic libraries may be useful for extension of sequence into 5' non-transcribed regulatory regions.

Capillary electrophoresis systems which are commercially available may be used to analyze the size or confirm the nucleotide sequence of sequencing or PCR products. In particular, capillary sequencing may employ flowable polymers for electrophoretic separation, four different nucleotide-specific, laser-stimulated fluorescent dyes, and a charge coupled device camera for detection of the emitted wavelengths. Output/light intensity may be converted to electrical signal using appropriate software (e.g., Genotyper™ and Sequence Navigator™, Perkin Elmer), and the entire process from loading of samples to computer analysis and electronic data display may be computer controlled. Capillary electrophoresis is especially preferable for sequencing small DNA fragments which may be present in limited amounts in a particular sample.

In another embodiment of the invention, polynucleotide sequences or fragments thereof which encode GAPIP may be cloned in recombinant DNA molecules that direct expression of GAPIP, or fragments or functional equivalents thereof, in appropriate host cells. Due to the inherent degeneracy of the genetic code, other DNA sequences which encode substantially the same or a functionally equivalent amino acid sequence may be produced and used to express GAPIP.

The nucleotide sequences of the present invention can be engineered using methods generally known in the art in order to alter GAPIP-encoding sequences for a variety of purposes including, but not limited to, modification of the cloning, processing, and/or expression of the gene product. DNA shuffling by random fragmentation and PCR reassembly of gene fragments and synthetic oligonucleotides may be used to engineer the nucleotide sequences. For example, oligonucleotide-mediated site-directed mutagenesis may be used to introduce mutations that create new restriction sites, alter glycosylation patterns, change codon preference, produce splice variants, and so forth.

In another embodiment, sequences encoding GAPIP may be synthesized, in whole or in part, using chemical methods well known in the art. (See, e.g., Caruthers, M. H. et al. (1980) Nucl. Acids Res. Symp. Ser. 215–223, and Horn, T. et al. (1980) Nucl. Acids Res. Symp. Ser. 225–232.) Alternatively, GAPIP itself or a fragment thereof may be synthesized using chemical methods. For example, peptide synthesis can be performed using various solid-phase techniques. (See, e.g., Roberge, J. Y. et al. (1995) Science 269:202–204.) Automated synthesis may be achieved using the ABI 431 A Peptide Synthesizer (Perkin Elmer). Additionally, the amino acid sequence of GAPIP, or any part thereof, may be altered during direct synthesis and/or combined with sequences from other proteins, or any part thereof, to produce a variant polypeptide.

The peptide may be substantially purified by preparative high performance liquid chromatography. (See, e.g, Chiez, R. M. and F. Z. Regnier (1990) Methods Enzymol. 182:392–421.) The composition of the synthetic peptides may be confirmed by amino acid analysis or by sequencing. (See, e.g., Creighton, T. (1984) *Proteins, Structures and Molecular Properties*, WH Freeman and Co., New York, N.Y.)

In order to express a biologically active GAPIP, the nucleotide sequences encoding GAPIP or derivatives thereof may be inserted into an appropriate expression vector, i.e., a vector which contains the necessary elements for transcriptional and translational control of the inserted coding sequence in a suitable host. These elements include regulatory sequences, such as enhancers, constitutive and inducible promoters, and 5' and 3' untranslated regions in the vector and in polynucleotide sequences encoding GAPIP. Such elements may vary in their strength and specificity. Specific initiation signals may also be used to achieve more efficient translation of sequences encoding GAPIP. Such signals include the ATG initiation codon and adjacent sequences, e.g. the Kozak sequence. In cases where sequences encoding GAPIP and its initiation codon and upstream regulatory sequences are inserted into the appropriate expression vector, no additional transcriptional or translational control signals may be needed. However, in cases where only coding sequence, or a fragment thereof, is inserted, exogenous translational control signals including an in-frame ATG initiation codon should be provided by the vector. Exogenous translational elements and initiation codons may be of various origins, both natural and synthetic. The efficiency of expression may be enhanced by the inclusion of enhancers appropriate for the particular host cell system used. (See, e.g., Scharf, D. et al. (1994) Results Probi. Cell Differ. 20:125–162.) Methods which are well known to those skilled in the art may be used to construct expression vectors containing sequences encoding GAPIP and appropriate transcriptional and translational control elements. These methods include in vitro recombinant DNA techniques, synthetic techniques, and in vivo genetic recombination. (See, e.g., Sambrook, J. et al. (1989) *Molecular Cloning, A Laboratory Manual*, Cold Spring Harbor Press, Plainview, N.Y., ch. 4, 8, and 16–17; and Ausubel, FM. et al. (1995, and periodic supplements) *Current Protocols in Molecular Biology*, John Wiley & Sons, New York, N.Y., ch. 9, 13, and 16.)

A variety of expression vector/host systems may be utilized to contain and express sequences encoding GAPIP. These include, but are not limited to, microorganisms such as bacteria transformed with recombinant bacteriophage, plasmid, or cosmid DNA expression vectors; yeast transformed with yeast expression vectors; insect cell systems infected with viral expression vectors (e.g., baculovirus); plant cell systems transformed with viral expression vectors (e.g., cauliflower mosaic virus (CaMV) or tobacco mosaic virus (TMV)) or with bacterial expression vectors (e.g., Ti or pBR322 plasmids); or animal cell systems. The invention is not limited by the host cell employed.

In bacterial systems, a number of cloning and expression vectors may be selected depending upon the use intended for polynucleotide sequences encoding GAPIP. For example, routine cloning, subcloning, and propagation of polynucleotide sequences encoding GAPIP can be achieved using a multifunctional *E. coli* vector such as Bluescript® (Stratagene) or pSport1™ plasmid (GIBCO BRL). Ligation of sequences encoding GAPIP into the vector's multiple cloning site disrupts the lacZ gene, allowing a colorimetric screening procedure for identification of transformed bacteria containing recombinant molecules. In addition, these vectors may be useful for in vitro transcription, dideoxy sequencing, single strand rescue with helper phage, and creation of nested deletions in the cloned sequence. (See, e.g., Van Heeke, G. and S. M. Schuster (1989) J. Biol. Chem. 264:5503–5509.) When large quantities of GAPIP are needed, e.g. for the production of antibodies, vectors which direct high level expression of GAPIP may be used. For example, vectors containing the strong, inducible T5 or T7 bacteriophage promoter may be used.

Yeast expression systems may be used for production of GAPIP. A number of vectors containing constitutive or inducible promoters, such as alpha factor, alcohol oxidase, and PGH, may be used in the yeast *Saccharomyces cerevisiae* or *Pichia pastoris*. In addition, such vectors direct either the secretion or intracellular retention of expressed proteins and enable integration of foreign sequences into the host genome for stable propagation. (See, e.g., Ausubel, supra; and Grant et al. (1987) Methods Enzymol. 153:516–54; Scorer, C. A. et al. (1994) Bio/Technology 12:181–184.)

Plant systems may also be used for expression of GAPIP. Transcription of sequences encoding GAPIP may be driven viral promoters, e.g., the 35S and 19S promoters of CaMV used alone or in combination with the omega leader sequence from TMV. (Takamatsu, N. (1987) EMBO J. 6:307–311.) Alternatively, plant promoters such as the small subunit of RUBISCO or heat shock promoters may be used. (See, e.g., Coruzzi, G. et al. (1984) EMBO J. 3:1671–1680; Broglie, R. et al. (1984) Science 224:838–843; and Winter,. J. et al. (1991) Results Probl. Cell Differ. 17:85–105.) These constructs can be introduced into plant cells by direct DNA transformation or pathogen-mediated transfection. (See, e.g., Hobbs, S. or Murry, L. E. in *McGraw Hill Yearbook of Science and Technology* (1992) McGraw Hill, New York, N.Y.; pp. 191–196.)

In mammalian cells, a number of viral-based expression systems may be utilized. In cases where an adenovirus is used as an expression vector, sequences encoding GAPIP may be ligated into an adenovirus transcription/translation complex consisting of the late promoter and tripartite leader sequence. Insertion in a non-essential E1 or E3 region of the viral genome may be used to obtain infective virus which expresses GAPIP in host cells. (See, e.g., Logan, J. and T. Shenk (1984) Proc. Natl. Acad. Sci. 81:3655–3659.) In addition, transcription enhancers, such as the Rous sarcoma virus (RSV) enhancer, may be used to increase expression in mammalian host cells. SV40 or EBV-based vectors may also be used for high-level protein expression.

Human artificial chromosomes (HACs) may also be employed to deliver larger fragments of DNA than can be contained in and expressed from a plasmid. HACs of about 6 kb to 10 Mb are constructed and delivered via conventional delivery methods (liposomes, polycationic amino polymers, or vesicles) for therapeutic purposes.

For long term production of recombinant proteins in mammalian systems, stable expression of GAPIP in cell lines is preferred. For example, sequences encoding GAPIP can be transformed into cell lines using expression vectors which may contain viral origins of replication and/or endogenous expression elements and a selectable marker gene on the same or on a separate vector. Following the introduction of the vector, cells may be allowed to grow for about 1 to 2 days in enriched media before being switched to selective media. The purpose of the selectable marker is to confer resistance to a selective agent, and its presence allows growth and recovery of cells which successfully express the introduced sequences. Resistant clones of stably transformed cells may be propagated using tissue culture techniques appropriate to the cell type.

Any number of selection systems may be used to recover transformed cell lines. These include, but are not limited to, the herpes simplex virus thymidine kinase and adenine phosphoribosyltransferase genes, for use in tk⁻ or apr⁻ cells, respectively. (See, e.g., Wigler, M. et al. (1977) Cell 11:223–232; and Lowy, I. et al. (1980) Cell 22:817–823.) Also, antimetabolite, antibiotic, or herbicide resistance can be used as the basis for selection. For example, dhfr confers resistance to methotrexate; neo confers resistance to the aminoglycosides neomycin and G-418; and als or pat confer resistance to chlorsulfuron and phosphinotricin acetyltransferase, respectively. (See, e.g., Wigler, M. et al. (1980) Proc. Natl. Acad. Sci. 77:3567–3570; Colbere-Garapin, F. et al (1981) J. Mol. Biol. 150:1–14; and Murry, supra.) Additional selectable genes have been described, e.g., trpB and hisD, which alter cellular requirements for metabolites. (See, e.g., Hartman, S. C. and R. C. Mulligan (1988) Proc. Natl. Acad. Sci. 85:8047–8051.) Visible markers, e.g., anthocyanins, green fluorescent proteins (GFP) (Clontech, Palo Alto, Calif.), 3 glucuronidase and its substrate β-D-glucuronoside, or luciferase and its substrate luciferin may be used. These markers can be used not only to identify transformants, but also to quantify the amount of transient or stable protein expression attributable to a specific vector system. (See, e.g., Rhodes, C. A. et al. (1995) Methods Mol. Biol. 55:121–131.)

Although the presence/absence of marker gene expression suggests that the gene of interest is also present, the presence and expression of the gene may need to be confirmed. For example, if the sequence encoding GAPIP is inserted within a marker gene sequence, transformed cells containing sequences encoding GAPIP can be identified by the absence of marker gene function. Alternatively, a marker gene can be placed in tandem with a sequence encoding GAPIP under the control of a single promoter. Expression of the marker gene in response to induction or selection usually indicates expression of the tandem gene as well.

In general, host cells that contain the nucleic acid sequence encoding GAPIP and that express GAPIP may be identified by a variety of procedures known to those of skill in the art. These procedures include, but are not limited to, DNA-DNA or DNA-RNA hybridizations, PCR amplification, and protein bioassay or immunoassay techniques which include membrane, solution, or chip based technologies for the detection and/or quantification of nucleic acid or protein sequences.

Immunological methods for detecting and measuring the expression of GAPIP using either specific polyclonal or monoclonal antibodies are known in the art. Examples of such techniques include enzyme-linked immunosorbent assays (ELISAs), radioimmunoassays (RIAs), and fluorescence activated cell sorting (FACS). A two-site, monoclonal-based immunoassay utilizing monoclonal antibodies reactive to two non-interfering epitopes on GAPIP is preferred, but a competitive binding assay may be employed. These and other assays are well known in the art. (See, e.g., Hampton, R. et al. (1990) Serological Methods, a Laboratory Manual, APS Press, St Paul, Minn., Section IV; Coligan, J. E. et al. (1997 and periodic supplements) Current Protocols in Immunology, Greene Pub. Associates and Wiley-Interscience, New York, N.Y.; and Maddox, D. E. et al. (1983) J. Exp. Med. 158:1211–1216).

A wide variety of labels and conjugation techniques are known by those skilled in the art and may be used in various nucleic acid and amino acid assays. Means for producing labeled hybridization or PCR probes for detecting sequences related to polynucleotides encoding GAPIP include oligolabeling, nick translation, end-labeling, or PCR amplification using a labeled nucleotide. Alternatively, the sequences encoding GAPIP, or any fragments thereof, may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits, such as those provided by Pharmacia & Upjohn (Kalamazoo, Mich.), Promega (Madison, Wis.), and U.S. Biochemical Corp. (Cleveland, Ohio). Suitable reporter molecules or labels which may be used for ease of detection include radionuclides, enzymes, fluorescent, chemiluminescent, or chromogenic agents, as well as substrates, cofactors, inhibitors, magnetic particles, and the like.

Host cells transformed with nucleotide sequences encoding GAPIP may be cultured under conditions suitable for the expression and recovery of the protein from cell culture. The protein produced by a transformed cell may be secreted or retained intracellularly depending on the sequence and/or the vector used. As will be understood by those of skill in the art, expression vectors containing polynucleotides which encode GAPIP may be designed to contain signal sequences which direct secretion of GAPIP through a prokaryotic or eukaryotic cell membrane.

In addition, a host cell strain may be chosen for its ability to modulate expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to specify protein targeting, folding, and/or activity. Different host cells which have specific cellular machinery and characteristic mechanisms for post-translational activities (e.g., CHO, HeLa, MDCK, HEK293, and W138), are available from the American Type Culture Collection (ATCC, Bethesda, Md.) and may be chosen to ensure the correct modification and processing of the foreign protein.

In another embodiment of the invention, natural, modified, or recombinant nucleic acid sequences encoding GAPIP may be ligated to a heterologous sequence resulting in translation of a fusion protein in any of the aforementioned host systems. For example, a chimeric GAPIP protein containing a heterologous moiety that can be recognized by a commercially available antibody may facilitate the screening of peptide libraries for inhibitors of GAPIP activity. Heterologous protein and peptide moieties may also facilitate purification of fusion proteins using commercially available affinity matrices. Such moieties include, but are not limited to, glutathione S-transferase (GST), maltose binding protein (MBP), thioredoxin (Trx), calmodulin binding peptide (CBP), 6-His, FLAG, c-myc, and hemagglutinin (HA). GST, MBP, Trx, CBP, and 6-His enable purification of their cognate fusion proteins on immobilized glutathione, maltose, phenylarsine oxide, calmodulin, and metal-chelate resins, respectively. FLAG, c-myc, and hemagglutinin (HA) enable immunoaffinity purification of fusion proteins using commercially available monoclonal and polyclonal antibodies that specifically recognize these epitope tags. A fusion protein may also be engineered to contain a proteolytic cleavage site located between the GAPIP encoding sequence and the heterologous protein sequence, so that GAPIP may be cleaved away from the heterologous moiety following purification. Methods for fusion protein expression and purification are discussed in Ausubel, F. M. et al. (1995 and periodic supplements) Current Protocols in Molecular Biology, John Wiley & Sons, New York, N.Y., ch 10. A variety of commercially available kits may also be used to facilitate expression and purification of fusion proteins.

In a further embodiment of the invention, synthesis of radiolabeled GAPIP may be achieved in vitro using the TNT™ rabbit reticulocyte lysate or wheat germ extract systems (Promega, Madison, Wis.). These systems couple transcription and translation of protein-coding sequences operably associated with the T7, T3, or SP6 promoters. Translation takes place in the presence of a radiolabeled amino acid precursor, preferably $^{35}$S-methionine.

Fragments of GAPIP may be produced not only by recombinant production, but also by direct peptide synthesis using solid-phase techniques. (See, e.g., Creighton, supra pp. 55–60.) Protein synthesis may be performed by manual techniques or by automation. Automated synthesis may be achieved, for example, using the Applied Biosystems 431 A Peptide Synthesizer (Perkin Elmer). Various fragments of GAPIP may be synthesized separately and then combined to produce the full length molecule.

Therapeutics

Chemical and structural similarity exists among GAPIP and human pre-inter-α-trypsin inhibitor (GI 33985; SEQ ID NO:3), human pre-inter-α-trypsin inhibitor heavy chain H1 (GI 33989; SEQ ID NO:4), and human pre-inter-α-trypsin inhibitor heavy chain H3 (GI 288563; SEQ ID NO:5). In addition, GAPIP is expressed in cancer, immune, reproductive, gastrointestinal, nervous, and fetal tissues. Therefore, GAPIP appears to play a role in reproductive, developmental, neoplastic, and immunological disorders.

Therefore, in one embodiment, a pharmaceutical composition comprising a substantially purified GAPIP in conjunction with a suitable pharmaceutical carrier may be administered to a subject to treat or prevent a reproductive disorder. Such reproductive disorders can include, but are not limited to, disorders of prolactin production; infertility, including tubal disease, ovulatory defects, and endometriosis; disruptions of the estrous cycle, disruptions of the menstrual cycle, polycystic ovary syndrome, ovarian hyperstimulation syndrome, endometrial and ovarian tumors, uterine fibroids, autoimmune disorders, ectopic pregnancies, and teratogenesis; cancer of the breast, fibrocystic breast disease, and galactorrhea; disruptions of spermatogenesis, abnormal sperm physiology, cancer of the testis, cancer of the prostate, benign prostatic hyperplasia, prostatitis, Peyronie's disease, carcinoma of the male breast, and gynecomastia.

In another embodiment, a vector capable of expressing GAPIP or a fragment or derivative thereof may be administered to a subject to treat or prevent a reproductive disorder including, but not limited to, those described above.

In a further embodiment, GAPIP or a fragment or derivative thereof may be administered to a subject to treat or prevent a reproductive disorder including, but not limited to, those provided above.

In still another embodiment, an agonist which modulates the activity of GAPIP may be administered to a subject to treat or prevent a reproductive disorder including, but not limited to, those listed above.

In one embodiment, a pharmaceutical composition comprising a substantially purified GAPIP in conjunction with a suitable pharmaceutical carrier may be administered to a subject to treat or prevent a developmental disorder. The term "developmental disorder" refers to any disorder associated with growth and differentiation, embryogenesis, and morphogenesis involving any tissue, organ, or system of a subject (such as the brain, adrenal gland, kidney, skeletal or reproductive system). Such developmental disorders can include, but are not limited to, renal tubular acidosis, anemia, Cushing's syndrome, achondroplastic dwarfism, Duchenne and Becker muscular dystrophy, epilepsy, gonadal dysgenesis, WAGR syndrome (Wilms' tumor, aniridia, genitourinary abnormalities, and mental retardation), Smith-Magenis syndrome, myelodysplastic syndrome, hereditary mucoepithelial dysplasia, hereditary keratodermas, hereditary neuropathies such as Charcot-Marie-Tooth disease and neurofibromatosis, hypothyroidism, hydrocephalus, seizure disorders such as Syndenham's chorea and cerebral palsy, spinal bifida, congenital glaucoma, cataract, and sensorineural hearing loss.

In another embodiment, a vector capable of expressing GAPIP or a fragment or derivative thereof may be administered to a subject to treat or prevent a developmental disorder including, but not limited to, those described above.

In a further embodiment, GAPIP or a fragment or derivative thereof may be administered to a subject to treat or prevent a developmental disorder including, but not limited to, those provided above.

In still another embodiment, an agonist which modulates the activity of GAPIP may be administered to a subject to treat or prevent a developmental disorder including, but not limited to, those listed above.

In one embodiment, an antagonist of GAPIP may be administered to a subject to treat or prevent a neoplastic disorder. Such neoplastic disorders may include, but are not limited to, adenocarcinoma, leukemia, lymphoma, melanoma, myeloma, sarcoma, teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus. In one aspect, an antibody which specifically binds GAPIP may be used directly as an antagonist or indirectly as a targeting or delivery mechanism for bringing a pharmaceutical agent to cells or tissue which express GAPIP.

In an additional embodiment, a vector expressing the complement of the polynucleotide encoding GAPIP may be administered to a subject to treat or prevent a neoplastic disorder including, but not limited to, those described above.

In one embodiment, an antagonist of GAPIP may be administered to a subject to treat or prevent an immunological disorder. Such immunological disorders may include, but are not limited to, acquired immunodeficiency syndrome (AIDS), Addison's disease, adult respiratory distress syndrome, allergies, ankylosing spondylitis, amyloidosis, anemia, asthma, atherosclerosis, autoimmune hemolytic anemia, autoimmune thyroiditis, bronchitis, cholecystitis, contact dermatitis, Crohn's disease, atopic dermatitis, dermatomyositis, diabetes mellitus, emphysema, episodic lymphopenia with lymphocytotoxins, erythroblastosis fetalis, erythema nodosum, atrophic gastritis, glomerulonephritis, Goodpasture's syndrome, gout, Graves' disease, Hashimoto's thyroiditis, hypereosinophilia, irritable bowel syndrome, multiple sclerosis, myasthenia gravis, myocardial or pericardial inflammation, osteoarthritis, osteoporosis, pancreatitis, polymyositis, psoriasis, Reiter's syndrome, rheumatoid arthritis, scieroderma, Sjögren's syndrome, systemic anaphylaxis, systemic lupus erythematosus, systemic sclerosis, thrombocytopenic purpura, ulcerative colitis, uveitis, Werner syndrome, complications of cancer, hemodialysis, and extracorporeal circulation, viral, bacterial, fungal, parasitic, protozoal, and helminthic infections, and trauma; and arteriosclerosis, bursitis, cirrhosis, hepatitis, mixed connective tissue disease (MCTD), myelofibrosis, paroxysmal nocturnal hemoglobinuria, polycythemia vera, and primary thrombocythemia. In one aspect, an antibody which specifically binds GAPIP may be used directly as an antagonist or indirectly as a targeting or delivery mechanism for bringing a pharmaceutical agent to cells or tissue which express GAPIP.

In an additional embodiment, a vector expressing the complement of the polynucleotide encoding GAPIP may be administered to a subject to treat or prevent an immunological disorder including, but not limited to, those described above.

In other embodiments, any of the proteins, antagonists, antibodies, agonists, complementary sequences, or vectors of the invention may be administered in combination with other appropriate therapeutic agents. Selection of the appropriate agents for use in combination therapy may be made by one of ordinary skill in the art, according to conventional pharmaceutical principles. The combination of therapeutic agents may act synergistically to effect the treatment or prevention of the various disorders described above. Using this approach, one may be able to achieve therapeutic efficacy with lower dosages of each agent, thus reducing the potential for adverse side effects.

An antagonist of GAPIP may be produced using methods which are generally known in the art. In particular, purified GAPIP may be used to produce antibodies or to screen libraries of pharmaceutical agents to identify those which specifically bind GAPIP. Antibodies to GAPIP may also be generated using methods that are well known in the art. Such antibodies may include, but are not limited to, polyclonal, monoclonal, chimeric, and single chain antibodies, Fab fragments, and fragments produced by a Fab expression library. Neutralizing antibodies (i.e., those which inhibit dimer formation) are especially preferred for therapeutic use.

For the production of antibodies, various hosts including goats, rabbits, rats, mice, humans, and others may be immunized by injection with GAPIP or with any fragment or oligopeptide thereof which has immunogenic properties. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, KLH, and dinitrophenol. Among adjuvants used in humans, BCG (bacilli Calmette-Guerin) and *Corynebacterium parvum* are especially preferable.

It is preferred that the oligopeptides, peptides, or fragments used to induce antibodies to GAPIP have an amino acid sequence consisting of at least about 5 amino acids, and, more preferably, of at least about 10 amino acids. It is also preferable that these oligopeptides, peptides, or fragments are identical to a portion of the amino acid sequence of the natural protein and contain the entire amino acid sequence of a small, naturally occurring molecule.

Short stretches of GAPIP amino acids may be fused with those of another protein, such as KLH, and antibodies to the chimeric molecule may be produced.

Monoclonal antibodies to GAPIP may be prepared using any technique which provides for the production of antibody molecules by continuous cell lines in culture. These include, but are not limited to, the hybridoma technique, the human B-cell hybridoma technique, and the EBV-hybridoma technique. (See, e.g., Kohler, G. et al. (1975) Nature 256:495–497; Kozbor, D. et al. (1985) J. Immunol. Methods 81:31–42; Cote, R. J. et al. (1983) Proc. Natl. Acad. Sci. 80:2026–2030; and Cole, S. P. et al. (1984) Mol. Cell Biol. 62:109–120.)

In addition, techniques developed for the production of "chimeric antibodies," such as the splicing of mouse antibody genes to human antibody genes to obtain a molecule with appropriate antigen specificity and biological activity, can be used. (See, e.g., Morrison, S. L. et al. (1984) Proc. Natl. Acad. Sci. 81:6851–6855; Neuberger, M. S. et al. (1984) Nature 312:604–608; and Takeda, S. et al. (1985) Nature 314:452–454.) Alternatively, techniques described for the production of single chain antibodies may be adapted, using methods known in the art, to produce GAPIP-specific single chain antibodies. Antibodies with related specificity, but of distinct idiotypic composition, may be generated by chain shuffling from random combinatorial immunoglobulin libraries. (See, e.g., Burton D. R. (1991) Proc. Natl. Acad. Sci. 88:10134–10137.)

Antibodies may also be produced by inducing in vivo production in the lymphocyte population or by screening immunoglobulin libraries or panels of highly specific binding reagents as disclosed in the literature. (See, e.g., Orlandi, R. et al. (1989) Proc. Natl. Acad. Sci. 86: 3833–3837; and Winter, G. et al. (1991) Nature 349:293–299.)

Antibody fragments which contain specific binding sites for GAPIP may also be generated. For example, such fragments include, but are not limited to, F(ab')2 fragments produced by pepsin digestion of the antibody molecule and Fab fragments generated by reducing the disulfide bridges of the F(ab')2 fragments. Alternatively, Fab expression libraries may be constructed to allow rapid and easy identification of monoclonal Fab fragments with the desired specificity. (See, e.g., Huse, W. D. et al. (1989) Science 246:1275–1281.)

Various immunoassays may be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between GAPIP and its specific antibody. A two-site, monoclonal-based immunoassay utilizing monoclonal antibodies reactive to two non-interfering GAPIP epitopes is preferred, but a competitive binding assay may also be employed. (Maddox, supra.)

In another embodiment of the invention, the polynucleotides encoding GAPIP, or any fragment or complement thereof, may be used for therapeutic purposes. In one aspect, the complement of the polynucleotide encoding GAPIP may be used in situations in which it would be desirable to block the transcription of the mRNA. In particular, cells may be transformed with sequences complementary to polynucleotides encoding GAPIP. Thus, complementary molecules or fragments may be used to modulate GAPIP activity, or to regulation of gene function. Such technology is now well known in the art, and sense or antisense oligonucleotides or larger fragments can be designed from various locations along the coding or control regions of sequences encoding GAPIP.

Expression vectors derived from retroviruses, adenoviruses, or herpes or vaccinia viruses, or from various bacterial plasmids, may be used for delivery of nucleotide sequences to the targeted organ, tissue, or cell population. Methods which are well known to those skilled in the art can be used to construct vectors to express nucleic acid sequences complementary to the polynucleotides encoding GAPIP. (See, e.g., Sambrook, supra; and Ausubel, supra.)

Genes encoding GAPIP can be turned off by transforming a cell or tissue with expression vectors which express high levels of a polynucleotide, or fragment thereof, encoding GAPIP. Such constructs may be used to introduce untranslatable sense or antisense sequences into a cell. Even in the absence of integration into the DNA, such vectors may continue to transcribe RNA molecules until they are disabled by endogenous nucleases. Transient expression may last for a month or more with a non-replicating vector, and may last even longer if appropriate replication elements are part of the vector system.

As mentioned above, modifications of gene expression can be obtained by designing complementary sequences or antisense molecules (DNA, RNA, or PNA) to the control, 5', or regulatory regions of the gene encoding GAPIP. Oligonucleotides derived from the transcription initiation site, e.g., between about positions −10 and +10 from the start site, are preferred. Similarly, inhibition can be achieved using triple helix base-pairing methodology. Triple helix pairing is useful because it causes inhibition of the ability of the double helix to open sufficiently for the binding of polymerases, transcription factors, or regulatory molecules. Recent therapeutic advances using triplex DNA have been described in the literature. (See, e.g., Gee, J. E. et al. (1994) in Huber, B. E. and B. I. Carr, *Molecular and Immunologic Approaches*, Futura Publishing Co., Mt. Kisco, N.Y., pp. 163–177.) A complementary sequence or antisense molecule may also be designed to block translation of mRNA by preventing the transcript from binding to ribosomes.

Ribozymes, enzymatic RNA molecules, may also be used to catalyze the specific cleavage of RNA. The mechanism of ribozyme action involves sequence-specific hybridization of the ribozyme molecule to complementary target RNA, followed by endonucleolytic cleavage. For example, engineered hammerhead motif ribozyme molecules may specifically and efficiently catalyze endonucleolytic cleavage of sequences encoding GAPIP.

Specific ribozyme cleavage sites within any potential RNA target are initially identified by scanning the target molecule for ribozyme cleavage sites, including the following sequences: GUA, GUU, and GUC. Once identified, short RNA sequences of between 15 and 20 ribonucleotides, corresponding to the region of the target gene containing the cleavage site, may be evaluated for secondary structural features which may render the oligonucleotide inoperable. The suitability of candidate targets may also be evaluated by testing accessibility to hybridization with complementary oligonucleotides using ribonuclease protection assays.

Complementary ribonucleic acid molecules and ribozymes of the invention may be prepared by any method known in the art for the synthesis of nucleic acid molecules. These include techniques for chemically synthesizing oligonucleotides such as solid phase phosphoramidite chemical synthesis. Alternatively, RNA molecules may be generated by in vitro and in vivo transcription of DNA sequences encoding GAPIP. Such DNA sequences may be incorporated into a wide variety of vectors with suitable RNA polymerase promoters such as T7 or SP6. Alternatively, these cDNA constructs that synthesize complementary RNA, constitutively or inducibly, can be introduced into cell lines, cells, or tissues. RNA molecules may be modified to increase intracellular stability and half-life.

Possible modifications include, but are not limited to, the addition of flanking sequences at the 5' and/or 3' ends of the molecule, or the use of phosphorothioate or 2' O-methyl rather than phosphodiesterase linkages within the backbone of the molecule. This concept is inherent in the production of PNAs and can be extended in all of these molecules by the inclusion of nontraditional bases such as inosine, queosine, and wybutosine, as well as acetyl-, methyl-, thio-, and similarly modified forms of adenine, cytidine, guanine, thymine, and uridine which are not as easily recognized by endogenous endonucleases.

Many methods for introducing vectors into cells or tissues are available and equally suitable for use in vivo, in vitro, and ex vivo. For ex vivo therapy, vectors may be introduced into stem cells taken from the patient and clonally propagated for autologous transplant back into that same patient. Delivery by transfection, by liposome injections, or by polycationic amino polymers may be achieved using methods which are well known in the art. (See, e.g., Goldman, C. K. et al. (1997) Nature Biotechnology 15:462–466.)

Any of the therapeutic methods described above may be applied to any subject in need of such therapy, including, for example, mammals such as dogs, cats, cows, horses, rabbits, monkeys, and most preferably, humans.

An additional embodiment of the invention relates to the administration of a pharmaceutical or sterile composition, in conjunction with a pharmaceutically acceptable carrier, for any of the therapeutic effects discussed above. Such pharmaceutical compositions may consist of GAPIP, antibodies to GAPIP, and mimetics, agonists, antagonists, or inhibitors of GAPIP. The compositions may be administered alone or in combination with at least one other agent, such as a stabilizing compound, which may be administered in any sterile, biocompatible pharmaceutical carrier including, but not limited to, saline, buffered saline, dextrose, and water. The compositions may be administered to a patient alone, or in combination with other agents, drugs, or hormones.

The pharmaceutical compositions utilized in this invention may be administered by any number of routes including, but not limited to, oral, intravenous, intramuscular, intraarterial, intramedullary, intrathecal, intraventricular, transdermal, subcutaneous, intraperitoneal, intranasal, enteral, topical, sublingual, or rectal means.

In addition to the active ingredients, these pharmaceutical compositions may contain suitable pharmaceutically-acceptable carriers comprising excipients and auxiliaries which facilitate processing of the active compounds into preparations which can be used pharmaceutically. Further details on techniques for formulation and administration may be found in the latest edition of *Remington's Pharmaceutical Sciences* (Maack Publishing Co., Easton, Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combining active compounds with solid excipient and processing the resultant mixture of granules (optionally, after grinding) to obtain tablets or dragee cores. Suitable auxiliaries can be added, if desired. Suitable excipients include carbohydrate or protein fillers, such as sugars, including lactose, sucrose, mannitol, and sorbitol; starch from corn, wheat, rice, potato, or other plants; cellulose, such as methyl cellulose, hydroxypropylmethyl-cellulose, or sodium carboxymethylcellulose; gums, including arabic and tragacanth; and proteins, such as gelatin and collagen. If desired, disintegrating or solubilizing agents may be added, such as the cross-linked polyvinyl pyrrolidone, agar, and alginic acid or a salt thereof, such as sodium alginate.

Dragee cores may be used in conjunction with suitable coatings, such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations which can be used orally include push-fit capsules made of gelatin, as well as soft, sealed capsules made of gelatin and a coating, such as glycerol or sorbitol. Push-fit capsules can contain active ingredients mixed with fillers or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Pharmaceutical formulations suitable for parenteral administration may be formulated in aqueous solutions, preferably in physiologically compatible buffers such as Hanks' solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils, such as sesame oil, or synthetic fatty acid esters, such as ethyl oleate, triglycerides, or liposomes. Non-lipid polycationic amino polymers may also be used for delivery. Optionally, the suspension may also contain suitable stabilizers or agents to increase the solubility of the compounds and allow for the preparation of highly concentrated solutions.

For topical or nasal administration, penetrants appropriate to the particular barrier to be permeated are used in the formulation. Such penetrants are generally known in the art.

The pharmaceutical compositions of the present invention may be manufactured in a manner that is known in the art, e.g., by means of conventional mixing, dissolving, granulating, dragee-making, levigating, emulsifying, encapsulating, entrapping, or lyophilizing processes.

The pharmaceutical composition may be provided as a salt and can be formed with many acids, including but not limited to, hydrochloric, sulfuric, acetic, lactic, tartaric, malic, and succinic acid. Salts tend to be more soluble in aqueous or other protonic solvents than are the corresponding free base forms. In other cases, the preferred preparation may be a lyophilized powder which may contain any or all of the following: 1 mM to 50 mM histidine, 0.1% to 2% sucrose, and 2% to 7% mannitol, at a pH range of 4.5 to 5.5, that is combined with buffer prior to use.

After pharmaceutical compositions have been prepared, they can be placed in an appropriate container and labeled for treatment of an indicated condition. For administration of GAPIP, such labeling would include amount, frequency, and method of administration.

Pharmaceutical compositions suitable for use in the invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays, e.g., of neoplastic cells or in animal models such as mice, rats, rabbits, dogs, or pigs. An animal model may also be used to determine the appropriate concentration range and route of administration. Such information can then be used to determine useful doses and routes for administration in humans.

A therapeutically effective dose refers to that amount of active ingredient, for example GAPIP or fragments thereof, antibodies of GAPIP, and agonists, antagonists or inhibitors of GAPIP, which ameliorates the symptoms or condition. Therapeutic efficacy and toxicity may be determined by standard pharmaceutical procedures in cell cultures or with experimental animals, such as by calculating the $ED_{50}$ (the dose therapeutically effective in 50% of the population) or $LD_{50}$ (the dose lethal to 50% of the population) statistics. The dose ratio of toxic to therapeutic effects is the therapeutic index, and it can be expressed as the $LD_{50}/ED_{50}$ ratio. Pharmaceutical compositions which exhibit large therapeutic indices are preferred. The data obtained from cell culture assays and animal studies are used to formulate a range of dosage for human use. The dosage contained in such compositions is preferably within a range of circulating concentrations that includes the $ED_{50}$ with little or no toxicity. The dosage varies within this range depending upon the dosage form employed, the sensitivity of the patient, and the route of administration.

The exact dosage will be determined by the practitioner, in light of factors related to the subject requiring treatment. Dosage and administration are adjusted to provide sufficient levels of the active moiety or to maintain the desired effect. Factors which may be taken into account include the severity of the disease state, the general health of the subject, the age, weight, and gender of the subject, time and frequency of administration, drug combination(s), reaction sensitivities, and response to therapy. Long-acting pharmaceutical compositions may be administered every 3 to 4 days, every week, or biweekly depending on the half-life and clearance rate of the particular formulation.

Normal dosage amounts may vary from about 0.1 $\mu$g to 100,000 $\mu$g, up to a total dose of about 1 gram, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

Diagnostics

In another embodiment, antibodies which specifically bind GAPIP may be used for the diagnosis of disorders characterized by expression of GAPIP, or in assays to monitor patients being treated with GAPIP or agonists, antagonists, or inhibitors of GAPIP. Antibodies useful for diagnostic purposes may be prepared in the same manner as described above for therapeutics. Diagnostic assays for GAPIP include methods which utilize the antibody and a label to detect GAPIP in human body fluids or in extracts of cells or tissues. The antibodies may be used with or without modification, and may be labeled by covalent or non-covalent attachment of a reporter molecule. A wide variety of reporter molecules, several of which are described above, are known in the art and may be used.

A variety of protocols for measuring GAPIP, including ELISAs, RIAs, and FACS, are known in the art and provide a basis for diagnosing altered or abnormal levels of GAPIP expression. Normal or standard values for GAPIP expression are established by combining body fluids or cell extracts taken from normal mammalian subjects, preferably human, with antibody to GAPIP under conditions suitable for complex formation The amount of standard complex formation may be quantitated by various methods, preferably by photometric means. Quantities of GAPIP expressed in subject samples, control and disease from biopsied tissues are compared with the standard values. Deviation between standard and subject values establishes the parameters for diagnosing disease.

In another embodiment of the invention, the polynucleotides encoding GAPIP may be used for diagnostic purposes. The polynucleotides which may be used include oligonucleotide sequences, complementary RNA and DNA molecules, and PNAs. The polynucleotides may be used to detect and quantitate gene expression in biopsied tissues in which expression of GAPIP may be correlated with disease. The diagnostic assay may be used to determine absence, presence, and excess expression of GAPIP, and to monitor regulation of GAPIP levels during therapeutic intervention.

In one aspect, hybridization with PCR probes which are capable of detecting polynucleotide sequences, including genomic sequences, encoding GAPIP or closely related molecules may be used to identify nucleic acid sequences which encode GAPIP. The specificity of the probe, whether it is made from a highly specific region, e.g., the 5' regulatory region, or from a less specific region, e.g., a conserved motif, and the stringency of the hybridization or amplification (maximal, high, intermediate, or low), will determine whether the probe identifies only naturally occurring sequences encoding GAPIP, allelic variants, or related sequences.

Probes may also be used for the detection of related sequences, and should preferably have at least 50% sequence identity to any of the GAPIP encoding sequences. The hybridization probes of the subject invention may be DNA or RNA and may be derived from the sequence of SEQ ID NO:2 or from genomic sequences including promoters, enhancers, and introns of the GAPIP gene.

Means for producing specific hybridization probes for DNAs encoding GAPIP include the cloning of polynucleotide sequences encoding GAPIP or GAPIP derivatives into vectors for the production of mRNA probes. Such vectors are known in the art, are commercially available, and may be used to synthesize RNA probes in vitro by means of the addition of the appropriate RNA polymerases and the appropriate labeled nucleotides. Hybridization probes may be labeled by a variety of reporter groups, for example, by radionuclides such as $^{32}P$ or $^{35}S$, or by enzymatic labels, such as alkaline phosphatase coupled to the probe via avidin/biotin coupling systems, and the like.

Polynucleotide sequences encoding GAPIP may be used for the diagnosis of a disorder associated with expression of GAPIP. Examples of such a disorder include, but are not limited to, a reproductive disorder, such as, disorders of prolactin production; infertility, including tubal disease, ovulatory defects, and endometriosis; disruptions of the estrous cycle, disruptions of the menstrual cycle, polycystic ovary syndrome, ovarian hyperstimulation syndrome, endometrial and ovarian tumors, uterine fibroids, autoimmune disorders, ectopic pregnancies, and teratogenesis; cancer of the breast, fibrocystic breast disease, and galactorrhea; disruptions of spermatogenesis, abnormal sperm physiology, cancer of the testis, cancer of the prostate, benign prostatic hyperplasia, prostatitis, Peyronie's disease, carcinoma of the male breast, and gynecomastia; a developmental disorder, such as, renal tubular acidosis, anemia, Cushing's syndrome, achondroplastic dwarfism, Duchenne and Becker muscular dystrophy, epilepsy, gonadal dysgenesis, WAGR syndrome (Wilms' tumor, aniridia, genitourinary abnormalities, and mental retardation), Smith-Magenis syndrome, myelodysplastic syndrome, hereditary mucoepithelial dysplasia, hereditary keratodermas, hereditary neuropathies such as Charcot-Marie-Tooth disease and neurofibromatosis, hypothyroidism, hydrocephalus, seizure disorders such as Syndenham's chorea and cerebral palsy, spinal bifida, congenital glaucoma, cataract, and sensorineural hearing loss; a neoplastic disorder, such as, adenocarcinoma, leukemia, lymphoma, melanoma, myeloma, sarcoma, teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus; and an immunological disorder, such as, acquired immunodeficiency syndrome (AIDS), Addison's disease, adult respiratory distress syndrome, allergies, ankylosing spondylitis, amyloidosis, anemia, asthma, atherosclerosis, autoimmune hemolytic anemia, autoimmune thyroiditis, bronchitis, cholecystitis, contact dermatitis, Crohn's disease, atopic dermatitis, dermatomyositis, diabetes mellitus, emphysema, episodic lymphopenia with lymphocytotoxins, erythroblastosis fetalis, erythema nodosum, atrophic gastritis, glomerulonephritis, Goodpasture's syndrome, gout, Graves' disease, Hashimoto's thyroiditis, hypereosinophilia, irritable bowel syndrome, multiple sclerosis, myasthenia gravis, myocardial or pericardial inflammation, osteoarthritis, osteoporosis, pancreatitis, polymyositis, psoriasis, Reiter's syndrome, rheumatoid arthritis, scleroderma, Sjögren's syndrome, systemic anaphylaxis, systemic lupus erythematosus, systemic sclerosis, thrombocytopenic purpura, ulcerative colitis, uveitis, Werner syndrome, complications of cancer, hemodialysis, and extracorporeal circulation, viral, bacterial, fungal, parasitic, protozoal, and helminthic infections, and trauma; and arteriosclerosis, bursitis, cirrhosis, hepatitis, mixed connective tissue disease (MCTD), myelofibrosis, paroxysmal nocturnal hemoglobinuria, polycythemia vera, and primary thrombocythemia. The polynucleotide sequences encoding GAPIP may be used in Southern or Northern analysis, dot blot, or other membrane-based technologies; in PCR technologies; in dipstick, pin, and ELISA assays; and in microarrays utilizing fluids or tissues from patients to detect altered GAPIP expression. Such qualitative or quantitative methods are well known in the art.

In a particular aspect, the nucleotide sequences encoding GAPIP may be useful in assays that detect the presence of associated disorders, particularly those mentioned above. The nucleotide sequences encoding GAPIP may be labeled by standard methods and added to a fluid or tissue sample from a patient under conditions suitable for the formation of hybridization complexes. After a suitable incubation period, the sample is washed and the signal is quantitated and compared with a standard value. If the amount of signal in the patient sample is significantly altered in comparison to a control sample then the presence of altered levels of nucleotide sequences encoding GAPIP in the sample indicates the presence of the associated disorder. Such assays may also be used to evaluate the efficacy of a particular therapeutic treatment regimen in animal studies, in clinical trials, or to monitor the treatment of an individual patient.

In order to provide a basis for the diagnosis of a disorder associated with expression of GAPIP, a normal or standard profile for expression is established. This may be accomplished by combining body fluids or cell extracts taken from normal subjects, either animal or human, with a sequence, or a fragment thereof, encoding GAPIP, under conditions suitable for hybridization or amplification. Standard hybridization may be quantified by comparing the values obtained from normal subjects with values from an experiment in which a known amount of a substantially purified polynucleotide is used. Standard values obtained in this manner may be compared with values obtained from samples from patients who are symptomatic for a disorder. Deviation from standard values is used to establish the presence of a disorder.

Once the presence of a disorder is established and a treatment protocol is initiated, hybridization assays may be repeated on a regular basis to determine if the level of expression in the patient begins to approximate that which is observed in the normal subject. The results obtained from successive assays may be used to show the efficacy of treatment over a period ranging from several days to months.

With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Additional diagnostic uses for oligonucleotides designed from the sequences encoding GAPIP may involve the use of PCR. These oligomers may be chemically synthesized, generated enzymatically, or produced in vitro. Oligomers will preferably contain a fragment of a polynucleotide encoding GAPIP, or a fragment of a polynucleotide complementary to the polynucleotide encoding GAPIP, and will be employed under optimized conditions for identification of a specific gene or condition. Oligomers may also be employed under less stringent conditions for detection or quantitation of closely related DNA or RNA sequences.

Methods which may also be used to quantitate the expression of GAPIP include radiolabeling or biotinylating nucleotides, coamplification of a control nucleic acid, and interpolating results from standard curves. (See, e.g., Melby, P. C. et al. (1993) J. Immunol. Methods 159:235–244; and Duplaa, C. et al. (1993) Anal. Biochem. 22: 229–236.) The speed of quantitation of multiple samples may be accelerated by running the assay in an ELISA format where the oligomer of interest is presented in various dilutions and a spectrophotometric or colorimetric response gives rapid quantitation.

In further embodiments, oligonucleotides or longer fragments derived from any of the polynucleotide sequences described herein may be used as targets in a microarray. The microarray can be used to monitor the expression level of large numbers of genes simultaneously and to identify genetic variants, mutations, and polymorphisms. This information may be used to determine gene function, to understand the genetic basis of a disorder, to diagnose a disorder, and to develop and monitor the activities of therapeutic agents.

Microarrays may be prepared, used, and analyzed using methods known in the art. (See, e.g., Brennan, T. M. et al. (1995) U.S. Pat. No. 5,474,796; Schena, M. et al. (1996) Proc. Natl. Acad. Sci. 93:10614–10619; Baldeschweiler et al. (1995) PCT application WO95/251116; Shalon, D. et al. (1995) PCT application WO95/35505; Heller, R. A. et al. (1997) Proc. Natl. Acad. Sci. 94:2150–2155; and Heller, M. J. et al. (1997) U.S. Pat. No. 5,605,662.)

In another embodiment of the invention, nucleic acid sequences encoding GAPIP may be used to generate hybridization probes useful in mapping the naturally occurring genomic sequence. The sequences may be mapped to a particular chromosome, to a specific region of a chromosome, or to artificial chromosome constructions, e.g., human artificial chromosomes (HACs), yeast artificial chromosomes (YACs), bacterial artificial chromosomes (BACs), bacterial P1 constructions, or single chromosome cDNA libraries. (See, e.g., Price, C. M. (1993) Blood Rev. 7:127–134; and Trask, B. J. (1991) Trends Genet. 7:149–154.)

Fluorescent in situ hybridization (FISH) may be correlated with other physical chromosome mapping techniques and genetic map data. (See, e.g., Heinz-Ulrich, et al. (1995) in Meyers, R. A. (ed.) *Molecular Biology and Biotechnology*, VCH Publishers New York, N.Y., pp. 965–968.) Examples of genetic map data can be found in various scientific journals or at the Online Mendelian Inheritance in Man (OMIM) site. Correlation between the location of the gene encoding GAPIP on a physical chromosomal map and a specific disorder, or a predisposition to a specific disorder, may help define the region of DNA associated with that disorder. The nucleotide sequences of the invention may be used to detect differences in gene sequences among normal, carrier, and affected individuals.

In situ hybridization of chromosomal preparations and physical mapping techniques, such as linkage analysis using established chromosomal markers, may be used for extending genetic maps. Often the placement of a gene on the chromosome of another mammalian species, such as mouse, may reveal associated markers even if the number or arm of a particular human chromosome is not known. New sequences can be assigned to chromosomal arms by physical mapping. This provides valuable information to investigators searching for disease genes using positional cloning or other gene discovery techniques. Once the disease or syndrome has been crudely localized by genetic linkage to a particular genomic region, e.g., ataxia-telangiectasia to 11q22-23, any sequences mapping to that area may represent associated or regulatory genes for further investigation. (See, e.g., Gatti, R. A. et al. (1988) Nature 336:577–580.) The nucleotide sequence of the subject invention may also be used to detect differences in the chromosomal location due to translocation, inversion, etc., among normal, carrier, or affected individuals.

In another embodiment of the invention, GAPIP, its catalytic or immunogenic fragments, or oligopeptides thereof can be used for screening libraries of compounds in any of a variety of drug screening techniques. The fragment employed in such screening may be free in solution, affixed to a solid support, borne on a cell surface, or located intracellularly. The formation of binding complexes between GAPIP and the agent being tested may be measured.

Another technique for drug screening provides for high throughput screening of compounds having suitable binding affinity to the protein of interest. (See, e.g., Geysen, et al. (1984) PCT application WO84/03564.) In this method, large numbers of different small test compounds are synthesized on a solid substrate, such as plastic pins or some other surface. The test compounds are reacted with GAPIP, or fragments thereof, and washed. Bound GAPIP is then detected by methods well known in the art. Purified GAPIP can also be coated directly onto plates for use in the aforementioned drug screening techniques. Alternatively, non-neutralizing antibodies can be used to capture the peptide and immobilize it on a solid support.

In another embodiment, one may use competitive drug screening assays in which neutralizing antibodies capable of binding GAPIP specifically compete with a test compound for binding GAPIP. In this manner, antibodies can be used to detect the presence of any peptide which shares one or more antigenic determinants with GAPIP.

In additional embodiments, the nucleotide sequences which encode GAPIP may be used in any molecular biology techniques that have yet to be developed, provided the new techniques rely on properties of nucleotide sequences that are currently known, including, but not limited to, such properties as the triplet genetic code and specific base pair interactions.

The examples below are provided to illustrate the subject invention and are not included for the purpose of limiting the invention.

EXAMPLES

I. cDNA Library Construction

The UTRSNOT02 cDNA library was constructed from uterus tissue obtained from a 34-year old Caucasian female (specimen #0047A) during a vaginal hysterectomy. Pathology indicated no diagnostic abnormality in the uterus or cervix. However, the left ovarian tissue showed dilated follicular cystis, all embedded. Patient history included the diagnoses of dysmenorrhea, dyspareunia, hemorrhoids and alcohol use. The patient was not taking any medications. Family history included malignant stomach neoplasm in the mother; benign large bowel neoplasm in the father; congenital heart anomaly, irritable bowel syndrome, and ulcerative colitis in the siblings; colon cancer in the paternal aunt at age sixty and colon cancer in paternal uncle at age eleven; and cerebrovascular disease, type II diabetes, and depression in the grandparents.

The frozen tissue was homogenized and lysed using a Brinkmann Homogenizer Polytron PT-3000 (Brinkmann Instruments, Westbury, N.Y.) in guanidinium isothiocyanate solution. The lysate was centrifuged over a 5.7 M CsCl cushion using a Beckman SW28 rotor in a Beckman L8-70M Ultracentrifuge (Beckman Instruments) for 18 hours at 25,000 rpm at ambient temperature. The RNA was extracted with acid phenol pH 4.7, precipitated using 0.3 M sodium acetate and 2.5 volumes of ethanol, resuspended in RNAse-free water, and DNase treated at 37° C. RNA extraction and precipitation were repeated as before. The mRNA was then isolated using the Qiagen Oligotex kit (QIAGEN, Inc., Chatsworth, Calif.) and used to construct the cDNA library.

The mRNA was handled according to the recommended protocols in the SuperScript Plasmid System for cDNA Synthesis and Plasmid Cloning (Catalog #18248-013, GIBCO-BRL). CDNA synthesis was initiated with a NotI-oligo d(T) primer. Double-stranded cDNA was blunted, ligated to SalI adaptors, digested with NotI, fractionated on a Sepharose CL4B column (Catalog #275105-01, Pharmacia), and those cDNAs exceeding 400 bp were ligated into the NotI and SalI sites of the pSport 1 vector. The plasmid pSport 1 was subsequently transformed into DH5aTM competent cells (Catalog #18258-012, GIBCO-BRL).

II Isolation and Sequencing of cDNA Clones

Plasmid DNA was released from the cells and purified using the REAL Prep 96 plasmid kit (Catalog #26173, QIAGEN, Inc.). The recommended protocol was employed except for the following changes: 1) the bacteria were cultured in 1 ml of sterile Terrific Broth (Catalog #22711, GIBCO-BRL) with carbenicillin at 25 mg/l and glycerol at 0.4%; 2) after inoculation, the cultures were incubated for 19 hours and at the end of incubation, the cells were lysed with 0.3 ml of lysis buffer; and 3) following isopropanol precipitation, the plasmid DNA pellet was resuspended in 0.1 ml of distilled water. After the last step in the protocol, samples were transferred to a 96-well block for storage at 4° C.

The cDNAs were sequenced by the method of Sanger et al. (1975, J. Mol. Biol. 94:441f), using a Hamilton Micro Lab 2200 (Hamilton, Reno, Nev.) in combination with Peltier Thermal Cyclers (PTC200 from MJ Research, Watertown, Mass.) and Applied Biosystems 377 DNA Sequencing Systems; and the reading frame was determined.

III. Similarity Searching of cDNA Clones and Their Deduced Proteins

The nucleotide sequences and/or amino acid sequences of the Sequence Listing were used to query sequences in the GenBank, SwissProt, BLOCKS, and Pima II databases. These databases, which contain previously identified and annotated sequences, were searched for regions of similarity using BLAST (Basic Local Alignment Search Tool). (See, e.g., Altschul, S. F. (1993) J. Mol. Evol 36:290–300; and Altschul et al. (1990) J. Mol. Biol. 215:403–410.)

BLAST produced alignments of both nucleotide and amino acid sequences to determine sequence similarity. Because of the local nature of the alignments, BLAST was especially useful in determining exact matches or in identifying homologs which may be of prokaryotic (bacterial) or eukaryotic (animal, fungal, or plant) origin. Other algorithms could have been used when dealing with primary sequence patterns and secondary structure gap penalties. (See, e.g., Smith, T. et al. (1992) Protein Engineering 5:35–51.) The sequences disclosed in this application have lengths of at least 49 nucleotides and have no more than 12% uncalled bases (where N is recorded rather than A, C, G, or T).

The BLAST approach searched for matches between a query sequence and a database sequence. BLAST evaluated the statistical significance of any matches found, and reported only those matches that satisfy the user-selected threshold of significance. In this application, threshold was set at $10^{25}$ for nucleotides and $10^{-8}$ for peptides.

Incyte nucleotide sequences were searched against the GenBank databases for primate (pri), rodent (rod), and other mammalian sequences (mam), and deduced amino acid sequences from the same clones were then searched against GenBank functional protein databases, mammalian (mamp), vertebrate (vrtp), and eukaryote (eukp), for similarity.

Additionally, sequences identified from cDNA libraries may be analyzed to identify those gene sequences encoding conserved protein motifs using an appropriate analysis program, e.g., BLOCKS. BLOCKS is a weighted matrix analysis algorithm based on short amino acid segments, or blocks, compiled from the PROSITE database. (Bairoch, A. et al. (1997) Nucleic Acids Res. 25:217–221.) The BLOCKS algorithm is useful for classifying genes with unknown functions. (Henikoff S. And Henikoff G. J., Nucleic Acids Research (1991) 19:6565–6572.) Blocks, which are 3–60 amino acids in length, correspond to the most highly conserved regions of proteins. The BLOCKS algorithm compares a query sequence with a weighted scoring matrix of blocks in the BLOCKS database. Blocks in the BLOCKS database are calibrated against protein sequences with known functions from the SWISS-PROT database to determine the stochastic distribution of matches. Similar databases such as PRINTS, a protein fingerprint database, are also searchable using the BLOCKS algorithm. (Attwood, T. K. et al. (1997) J. Chem. Inf. Comput. Sci. 37:417–424.) PRINTS is based on non-redundant sequences obtained from sources such as SWISS-PROT, GenBank, PIR, and NRL-3D.

The BLOCKS algorithm searches for matches between a query sequence and the BLOCKS or PRINTS database and evaluates the statistical significance of any matches found. Matches from a BLOCKS or PRINTS search can be evaluated on two levels, local similarity and global similarity. The degree of local similarity is measured by scores, and the extent of global similarity is measured by score ranking and probability values. A score of 1000 or greater for a BLOCKS match of highest ranking indicates that the match falls within the 0.5 percentile level of false positives when the matched block is calibrated against SWISS-PROT.

Likewise, a probability value of less than $1.0\times10^{-3}$ indicates that the match would occur by chance no more than one time in every 1000 searches. Only those matches with a cutoff score of 1000 or greater and a cutoff probability value of $1.0\times10^{-3}$ or less are considered in the functional analyses of the protein sequences in the Sequence Listing.

Nucleic and amino acid sequences of the Sequence Listing may also be analyzed using PFAM. PFAM is a Hidden Markov Model (HMM) based protocol useful in protein family searching. HMM is a probabilistic approach which analyzes consensus primary structures of gene families. (See, e.g., Eddy, S. R. (1996) Cur. Opin. Str. Biol. 6:361–365.)

The PFAM database contains protein sequences of 527 protein families gathered from publicly available sources, e.g., SWISS-PROT and PROSITE. PFAM searches for well characterized protein domain families using two high-quality alignment routines, seed alignment and full alignment. (See, e.g., Sonnhammer, E. L. L. et al. (1997) Proteins 28:405420.) The seed alignment utilizes the hmmls program, a program that searches for local matches, and a non-redundant set of the PFAM database. The full alignment utilizes the hmmfs program, a program that searches for multiple fragments in long sequences, e.g., repeats and motifs, and all sequences in the PFAM database. A result or score of 100 "bits" can signify that it is $2^{100}$-fold more likely that the sequence is a true match to the model or comparison sequence. Cutoff scores which range from 10 to 50 bits are generally used for individual protein families using the SWISS-PROT sequences as model or comparison sequences.

Two other algorithms, SIGPEPT and TM, both based on the HMM algorithm described above (see, e.g., Eddy, supra; and Sonnhammer, supra), identify potential signal sequences and transmembrane domains, respectively. SIGPEPT was created using protein sequences having signal sequence annotations derived from SWISS-PROT. It contains about 1413 non-redundant signal sequences ranging in length from 14 to 36 amino acid residues. TM was created similarly using transmembrane domain annotations. It contains about 453 non-redundant transmembrane sequences encompassing 1579 transmembrane domain segments. Suitable HMM models were constructed using the above sequences and were refined with known SWISS-PROT signal peptide sequences or transmembrane domain sequences until a high correlation coefficient, a measurement of the correctness of the analysis, was obtained. Using the protein sequences from the SWISS-PROT database as a test set, a cutoff score of 11 bits, as determined above, correlated with 91–94% true-positives and about 4.1% false-positives, yielding a correlation coefficient of about 0.87–0.90 for SIGPEPT. A score of 11 bits for TM will typically give the following results: 75% true positives; 1.72% false positives; and a correlation coefficient of 0.76. Each search evaluates the statistical significance of any matches found and reports only those matches that score at least 11 bits.

IV. Northern Analysis

Northern analysis is a laboratory technique used to detect the presence of a transcript of a gene and involves the hybridization of a labeled nucleotide sequence to a membrane on which RNAs from a particular cell type or tissue have been bound. (See, e.g., Sambrook, supra, ch. 7; and Ausubel, supra, ch. 4 and 16.)

Analogous computer techniques applying BLAST are used to search for identical or related molecules in nucleotide databases such as GenBank or LIFESEQ™ database (Incyte Pharmaceuticals). This analysis is much faster than multiple membrane-based hybridizations.

In addition, the sensitivity of the computer search can be modified to determine whether any particular match is categorized as exact or similar.

The basis of the search is the product score, which is defined as:

$$\frac{\% \text{ sequence identity} \times \% \text{ maximum BLAST score}}{100}$$

The product score takes into account both the degree of similarity between two sequences and the length of the sequence match. For example, with a product score of 40, the match will be exact within a 1% to 2% error, and, with a product score of 70, the match will be exact. Similar molecules are usually identified by selecting those which show product scores between 15 and 40, although lower scores may identify related molecules.

The results of Northern analysis are reported as a list of libraries in which the transcript encoding GAPIP occurs. Abundance and percent abundance are also reported. Abundance directly reflects the number of times a particular transcript is represented in a cDNA library, and percent abundance is abundance divided by the total number of sequences examined in the cDNA library.

V. Extension of GAPIP Encoding Polynucleotides

The nucleic acid sequence of Incyte Clone 688183 was used to design oligonucleotide primers for extending a partial nucleotide sequence to full length. One primer was synthesized to initiate extension of an antisense polynucleotide, and the other was synthesized to initiate extension of a sense polynucleotide. Primers were used to facilitate the extension of the known sequence "outward" generating amplicons containing new unknown nucleotide sequence for the region of interest. The initial primers were designed from the cDNA using OLIGO™ 4.06 (National Biosciences, Plymouth, Minn.), or another appropriate program, to be about 22 to 30 nucleotides in length, to have a GC content of about 50% or more, and to anneal to the target sequence at temperatures of about 68° C. to about 72° C. Any stretch of nucleotides which would result in hairpin structures and primer-primer dimerizations was avoided.

Selected human cDNA libraries (GIBCO-BRL) were used to extend the sequence. If more than one extension is necessary or desired, additional sets of primers are designed to further extend the known region.

High fidelity amplification was obtained by following the instructions for the XL-PCR™ kit (Perkin Elmer) and thoroughly mixing the enzyme and reaction mix. PCR was performed using the Peltier Thermal Cycler (PTC200; M.J. Research, Watertown, Mass.), beginning with 40 pmol of each primer and the recommended concentrations of all other components of the kit, with the following parameters:

| | |
|---|---|
| Step 1 | 94° C. for 1 min (initial denaturation) |
| Step 2 | 65° C. for 1 min |
| Step 3 | 68° C. for 6 min |
| Step 4 | 94° C. for 15 sec |
| Step 5 | 65° C. for 1 min |
| Step 6 | 68° C. for 7 min |
| Step 7 | Repeat steps 4 through 6 for an additional 15 cycles |
| Step 8 | 94° C. for 15 sec |
| Step 9 | 65° C. for 1 min |
| Step 10 | 68° C. for 7:15 min |
| Step 11 | Repeat steps 8 through 10 for an additional 12 cycles |
| Step 12 | 72° C. for 8 min |
| Step 13 | 4° C. (and holding) |

A 5 µl to 10 µl aliquot of the reaction mixture was analyzed by electrophoresis on a low concentration (about 0.6% to 0.8%) agarose mini-gel to determine which reactions were successful in extending the sequence. Bands thought to contain the largest products were excised from the gel, purified using QIAQUICK™ (QIAGEN Inc.), and trimmed of overhangs using Klenow enzyme to facilitate religation and cloning.

After ethanol precipitation, the products were redissolved in 13 µl of ligation buffer, 1 µl T4-DNA ligase (15 units) and 1 µl T4 polynucleotide kinase were added, and the mixture was incubated at room temperature for 2 to 3 hours, or overnight at 16° C. Competent E. coli cells (in 40 µl of appropriate media) were transformed with 3 µl of ligation mixture and cultured in 80 µl of SOC medium. (See, e.g., Sambrook, supra, Appendix A, p. 2.) After incubation for one hour at 37° C., the E. coli mixture was plated on Luria Bertani (LB) agar (See, e.g., Sambrook, supra, Appendix A, p. 1) containing carbenicillin (2× carb). The following day, several colonies were randomly picked from each plate and cultured in 150 µl of liquid LB/2× carb medium placed in an individual well of an appropriate commercially-available sterile 96-well microtiter plate. The following day, 5 µl of each overnight culture was transferred into a non-sterile 96-well plate and, after dilution 1:10 with water, 5 µl from each sample was transferred into a PCR array.

For PCR amplification, 18 µl of concentrated PCR reaction mix (3.3x) containing 4 units of rTth DNA polymerase, a vector primer, and one or both of the gene specific primers used for the extension reaction were added to each well. Amplification was performed using the following conditions:

| Step 1 | 94° C. for 60 sec |
| Step 2 | 94° C. for 20 sec |
| Step 3 | 55° C. for 30 sec |
| Step 4 | 72° C. for 90 sec |
| Step 5 | Repeat steps 2 through 4 for an additional 29 cycles |
| Step 6 | 72° C. for 180 sec |
| Step 7 | 4° C. (and holding) |

Aliquots of the PCR reactions were run on agarose gels together with molecular weight markers. The sizes of the PCR products were compared to the original partial cDNAs, and appropriate clones were selected, ligated into plasmid, and sequenced.

In like manner, the nucleotide sequence of SEQ ID NO:2 is used to obtain 5' regulatory sequences using the procedure above, oligonucleotides designed for 5' extension, and an appropriate genomic library.

VI. Labeling and Use of Individual Hybridization Probes

Hybridization probes derived from SEQ ID NO:2 are employed to screen cDNAs, genomic DNAs, or mRNAs. Although the labeling of oligonucleotides, consisting of about 20 base pairs, is specifically described, essentially the same procedure is used with larger nucleotide fragments. Oligonucleotides are designed using state-of-the-art software such as OLIGO™ 4.06 software (National Biosciences) and labeled by combining 50 pmol of each oligomer, 250 µCi of [γ-$^{32}$P] adenosine triphosphate (Amersham, Chicago, Ill.), and T4 polynucleotide kinase (DuPont NEN®, Boston, Mass.). The labeled oligonucleotides are substantially purified using a Sephadex™ G-25 superfine size exclusion dextran bead column (Pharmacia & Upjohn, Kalamazoo, Mich.). An aliquot containing $10^7$ counts per minute of the labeled probe is used in a typical membrane-based hybridization analysis of human genomic DNA digested with one of the following endonucleases: AseI, BglII, EcoRI, PstI, XbaI, or PvuII (DuPont NEN, Boston, Mass.).

The DNA from each digest is fractionated on a 0.7% agarose gel and transferred to nylon membranes (Nytran Plus, Schleicher & Schuell, Durham, N.H.). Hybridization is carried out for 16 hours at 40° C. To remove nonspecific signals, blots are sequentially washed at room temperature under increasingly stringent conditions up to 0.1× saline sodium citrate and 0.5% sodium dodecyl sulfate. After XOMAT AR™ film (Kodak, Rochester, N.Y.) is exposed to the blots to film for several hours, hybridization patterns are compared visually.

VII. Microarrays

A chemical coupling procedure and an ink jet device can be used to synthesize array elements on the surface of a substrate. (See, e.g., Baldeschweiler, supra.) An array analogous to a dot or slot blot may also be used to arrange and link elements to the surface of a substrate using thermal, UV, chemical, or mechanical bonding procedures. A typical array may be produced by hand or using available methods and machines and contain any appropriate number of elements. After hybridization, nonhybridized probes are removed and a scanner used to determine the levels and patterns of fluorescence. The degree of complementarity and the relative abundance of each probe which hybridizes to an element on the microarray may be assessed through analysis of the scanned images.

Full-length cDNAs, Expressed Sequence Tags (ESTs), or fragments thereof may comprise the elements of the microarray. Fragments suitable for hybridization can be selected using software well known in the art such as LASERGENE™. Full-length cDNAs, ESTs, or fragments thereof corresponding to one of the nucleotide sequences of the present invention, or selected at random from a cDNA library relevant to the present invention, are arranged on an appropriate substrate, e.g., a glass slide. The cDNA is fixed to the slide using, e.g., UV cross-linking followed by thermal and chemical treatments and subsequent drying. (See, e.g., Schena, M. et al. (1995) Science 270:467–470; and Shalon, D. et al. (1996) Genome Res. 6:639–645.) Fluorescent probes are prepared and used for hybridization to the elements on the substrate. The substrate is analyzed by procedures described above.

VIII. Complementary Polynucleotides

Sequences complementary to the GAPIP-encoding sequences, or any parts thereof, are used to detect, decrease, or inhibit expression of naturally occurring GAPIP. Although use of oligonucleotides comprising from about 15 to 30 base pairs is described, essentially the same procedure is used with smaller or with larger sequence fragments. Appropriate oligonucleotides are designed using OLIGO™ 4.06 software and the coding sequence of GAPIP. To inhibit transcription, a complementary oligonucleotide is designed from the most unique 5' sequence and used to prevent promoter binding to the coding sequence. To inhibit translation, a complementary oligonucleotide is designed to prevent ribosomal binding to the GAPIP-encoding transcript.

IX. Expression of GAPIP

Expression and purification of GAPIP is achieved using bacterial or virus-based expression systems. For expression of GAPIP in bacteria, cDNA is subcloned into an appropriate vector containing an antibiotic resistance gene and an inducible promoter that directs high levels of cDNA transcription. Examples of such promoters include, but are not limited to, the trp-lac (tac) hybrid promoter and the T5 or T7 bacteriophage promoter in conjunction with the lac operator regulatory element. Recombinant vectors are transformed into suitable bacterial hosts, e.g., BL2 1 (DE3). Antibiotic resistant bacteria express GAPIP upon induction with isopropyl beta-D-thiogalactopyranoside (IPTG). Expression of GAPIP in eukaryotic cells is achieved by infecting insect or mammalian cell lines with recombinant *Autographica californica* nuclear polyhedrosis virus (AcMNPV), commonly known as baculovirus. The nonessential polyhedrin gene of baculovirus is replaced with cDNA encoding GAPIP by either homologous recombination or bacterial-mediated transposition involving transfer plasmid intermediates. Viral infectivity is maintained and the strong polyhedrin promoter drives high levels of cDNA transcription. Recombinant baculovirus is used to infect *Spodoptera frugiperda* (Sf9) insect cells in most cases, or human hepatocytes, in some cases. Infection of the latter requires additional genetic modifications to baculovirus. (See Engelhard, E. K. et al. (1994) Proc. Natl. Acad. Sci. USA 91:3224–3227; Sandig, V. et al. (1996) Hum. Gene Ther. 7:1937–1945.)

In most expression systems, GAPIP is synthesized as a fusion protein with, e.g., glutathione S-transferase (GST) or a peptide epitope tag, such as FLAG or 6-His, permitting rapid, single-step, affinity-based purification of recombinant fusion protein from crude cell lysates. GST, a 26-kilodalton enzyme from *Schistosoma japonicum*, enables the purification of fusion proteins on immobilized glutathione under conditions that maintain protein activity and antigenicity (Pharmacia, Piscataway, N.J.). Following purification, the GST moiety can be proteolytically cleaved from GAPIP at specifically engineered sites. FLAG, an 8-amino acid peptide, enables immunoaffinity purification using commercially available monoclonal and polyclonal anti-FLAG antibodies (Eastman Kodak, Rochester,N.Y.). 6-His, a stretch of six consecutive histidine residues, enables purification on metal-chelate resins (QIAGEN Inc, Chatsworth, Calif.). Methods for protein expression and purification are discussed in Ausubel, F. M. et al. (1995 and periodic supplements) Current Protocols in Molecular Biology, John Wiley & Sons, New York, N.Y., ch 10, 16. Purified GAPIP obtained by these methods can be used directly in the following activity assay.

X. Demonstration of GAPIP Activity

Protease inhibitory activity of GAPIP is measured by the inhibition of hydrolysis by trypsin of appropriate synthetic peptide substrates conjugated with various chromogenic molecules in which the degree of hydrolysis is quantitated by spectrophotometric (or fluorometric) absorption of the released chromophore (Beynon and Bond supra, pp.25–55). Peptide substrates are selected for optimal activity using prepared trypsin. Chromogens commonly used are 2-naphthylamine, 4-nitroaniline, and furylacrylic acid. Assays are performed at ambient temperature and contain an aliquot of trypsin, the appropriate substrate in a suitable buffer, and serial dilutions of purified GAPIP. Reactions are carried out in an optical cuvette and followed by the increase/decrease in absorbance or fluorescence of the chromogen released during hydrolysis of the peptide substrate. The baseline absorbance in the absence of GAPIP is proportional to the trypsin activity in the assay. Reduction in absorbance is proportional to the GAPIP activity in the assay.

XI. Functional Assays

GAPIP function is assessed by expressing the sequences encoding GAPIP at physiologically elevated levels in mammalian cell culture systems. cDNA is subcloned into a mammalian expression vector containing a strong promoter that drives high levels of cDNA expression. Vectors of choice include pCMV SPORT™ (Life Technologies, Gaithersburg, Md.) and pCR™ 3.1 (Invitrogen, Carlsbad, Calif., both of which contain the cytomegalovirus promoter. 5–10 μg of recombinant vector are transiently transfected into a human cell line, preferably of endothelial or hematopoietic origin, using either liposome formulations or electroporation. 1–2 μg of an additional plasmid containing sequences encoding a marker protein are co-transfected. Expression of a marker protein provides a means to distinguish transfected cells from nontransfected cells and is a reliable predictor of cDNA expression from the recombinant vector. Marker proteins of choice include, e.g., Green Fluorescent Protein (GFP) (Clontech, Palo Alto, Calif.), CD64, or a CD64-GFP fusion protein. Flow cytometry (FCM), an automated, laser optics-based technique, is used to identify transfected cells expressing GFP or CD64-GFP, and to evaluate properties, for example, their apoptotic state. FCM detects and quantifies the uptake of fluorescent molecules that diagnose events preceding or coincident with cell death. These events include changes in nuclear DNA content as measured by staining of DNA with propidium iodide; changes in cell size and granularity as measured by forward light scatter and 90 degree side light scatter; down-regulation of DNA synthesis as measured by decrease in bromodeoxyuridine uptake; alterations in expression of cell surface and intracellular proteins as measured by reactivity with specific antibodies; and alterations in plasma membrane composition as measured by the binding of fluorescein-conjugated Annexin V protein to the cell surface. Methods in flow cytometry are discussed in Ormerod, M. G. (1994) Flow Cytometry, Oxford, New York, N.Y.

The influence of GAPIP on gene expression can be assessed using highly purified populations of cells transfected with sequences encoding GAPIP and either CD64 or CD64-GFP. CD64 and CD64-GFP are expressed on the surface of transfected cells and bind to conserved regions of human immunoglobulin G (IgG). Transfected cells are efficiently separated from nontransfected cells using magnetic beads coated with either human IgG or antibody against CD64 (DYNAL, Lake Success, N.Y.). mRNA can be purified from the cells using methods well known by those of skill in the art. Expression of mRNA encoding GAPIP and other genes of interest can be analyzed by Northern analysis or microarray techniques.

XII. Production of GAPIP Specific Antibodies

GAPIP substantially purified using polyacrylamide gel electrophoresis (PAGE)(see, e.g., Harrington, M. G. (1990) Methods Enzymol. 182:488–495), or other purification techniques, is used to immunize rabbits and to produce antibodies using standard protocols.

Alternatively, the GAPIP amino acid sequence is analyzed using LASERGENE™ software (DNASTAR Inc.) to determine regions of high immunogenicity, and a corresponding oligopeptide is synthesized and used to raise antibodies by means known to those of skill in the art. Methods for selection of appropriate epitopes, such as those near the C-terminus or in hydrophilic regions are well described in the art. (See, e.g., Ausubel supra, ch. 11.)

Typically, oligopeptides 15 residues in length are synthesized using an Applied Biosystems Peptide Synthesizer Model 43 1A using fmoc-chemistry and coupled to KLH (Sigma, St. Louis, Mo.) by reaction with N-maleimidobenzoyl-N-hydroxysuccinimide ester (MBS) to increase immunogenicity. (See, e.g., Ausubel supra.) Rabbits are immunized with the oligopeptide-KLH complex in complete Freund's adjuvant. Resulting antisera are tested for antipeptide activity by, for example, binding the peptide to plastic, blocking with 1% BSA, reacting with rabbit antisera, washing, and reacting with radio-iodinated goat anti-rabbit IgG.

XIII. Purification of Naturally Occurring GAPIP Using Specific Antibodies

Naturally occurring or recombinant GAPIP is substantially purified by immunoaffinity chromatography using antibodies specific for GAPIP. An immunoaffinity column is constructed by covalently coupling anti-GAPIP antibody to an activated chromatographic resin, such as CNBr-activated Sepharose (Pharmacia & Upjohn). After the coupling, the resin is blocked and washed according to the manufacturer's instructions.

Media containing GAPIP are passed over the immunoaffinity column, and the column is washed under conditions that allow the preferential absorbance of GAPIP (e.g., high ionic strength buffers in the presence of detergent). The column is eluted under conditions that disrupt antibody/GAPIP binding (e.g., a buffer of pH 2 to pH 3, or a high concentration of a chaotrope, such as urea or thiocyanate ion), and GAPIP is collected.

XIV. Identification of Molecules Which Interact with GAPIP

GAPIP, or biologically active fragments thereof, are labeled with $^{125}$I Bolton-Hunter reagent. (See, e.g., Bolton et al. (1973) Biochem. J. 133:529.) Candidate molecules previously arrayed in the wells of a multi-well plate are incubated with the labeled GAPIP, washed, and any wells with labeled GAPIP complex are assayed. Data obtained using different concentrations of GAPIP are used to calculate values for the number, affinity, and association of GAPIP with the candidate molecules.

Various modifications and variations of the described methods and systems of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

---

What is claimed is:

1. A purified polypeptide comprising the amino acid sequence of SEQ ID NO: 1.

2. A purified polypeptide having at least 90% amino acid sequence identity to SEQ ID NO: 1, and which retains trypsin inhibitory activity.

3. A composition comprising the polypeptide of claim 1.

4. A method for using a protein to screen a plurality of other molecules or compounds for a molecule or compound which specifically binds the protein, the method comprising:

(a) combining the protein of claim 1 with the of molecules or compounds under conditions suitable to allow complex formation; and (b) detecting complex formation, wherein the presence of the complex identifies a molecule or compound which specifically binds the protein.

5. The method of claim 4, wherein the molecule or compound is selected from the group consisting of inhibitors, peptides and antibodies.

6. A method of using a protein or a fragment thereof to purify a molecule or compound which specifically binds the protein from a sample, the method comprising:

a) combining the protein or a fragment thereof of claim 1 with a sample under conditions to allow specific binding;

b) recovering the bound protein; and c) separating the protein from the molecule or compound, thereby obtaining purified molecule or compound.

* * * * *

UNITED STATES PATENT AND TRADEMARK OFFICE
CERTIFICATE OF CORRECTION

PATENT NO. : 6,228,991 B1
DATED : May 8, 2001
INVENTOR(S) : Jennifer L. Hillman, Karl J. Guegler, Chandra Patterson It is certified that error appears in the above-identified patent and that said Letters Patent is hereby corrected as shown below:

Column 63, claim 4,
Line 39, delete "of" between the words "the" and "molecules".

Signed and Sealed this

Eighth Day of January, 2002

Attest:

JAMES E. ROGAN
Attesting Officer     Director of the United States Patent and Trademark Office